(12) United States Patent
Fritz et al.

(10) Patent No.: US 6,358,994 B1
(45) Date of Patent: Mar. 19, 2002

(54) 2-ACYLAMINOPROPANAMINES AS TACHYKININ RECEPTOR ANTAGONISTS

(75) Inventors: James E Fritz, McCordsville; Philip A Hipskind, New Palestine; Stephen W Kaldor, Indianapolis; Karen L Lobb, Indianapolis; James A Nixon, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/463,855

(22) PCT Filed: Aug. 6, 1998

(86) PCT No.: PCT/US98/16333

§ 371 Date: Jan. 27, 2000

§ 102(e) Date: Jan. 27, 2000

(87) PCT Pub. No.: WO99/07677

PCT Pub. Date: Feb. 18, 1999

Related U.S. Application Data

(60) Provisional application No. 60/054,997, filed on Aug. 6, 1997.

(51) Int. Cl.[7] .............................................. A61K 31/405
(52) U.S. Cl. ...................... 514/415; 514/412; 548/455; 548/504; 548/506
(58) Field of Search ................................. 514/412, 415, 514/419; 548/455, 504, 506

(56) References Cited

U.S. PATENT DOCUMENTS

| | | | | |
|---|---|---|---|---|
| 5,278,316 A | * | 1/1994 | Horwell et al. ............. | 548/496 |
| 5,328,927 A | | 7/1994 | Lewis et al. ................ | 514/415 |
| 5,360,820 A | | 11/1994 | Hagan et al. ............... | 514/559 |
| 5,491,140 A | | 2/1996 | Bruns et al. ................ | 514/212 |
| 5,530,009 A | | 6/1996 | Cho et al. ................... | 514/316 |
| 5,554,627 A | | 9/1996 | Lewis et al. ................ | 514/305 |
| 5,594,022 A | | 1/1997 | Horwell et al. ............. | 514/419 |
| 5,652,369 A | | 7/1997 | Handa et al. ............... | 546/200 |

FOREIGN PATENT DOCUMENTS

| WO | WO 95/14017 | 5/1995 |
|---|---|---|

OTHER PUBLICATIONS

Chemical Abstract, vol. 122, Abstract No. 122:32016, for Horwell, et al., US 5,278,316.

* cited by examiner

*Primary Examiner*—Zohreh Fay
(74) *Attorney, Agent, or Firm*—Manisha A. Desai; Elizabeth A. Dawalt

(57) ABSTRACT

This invention provides compounds of the Formula I:

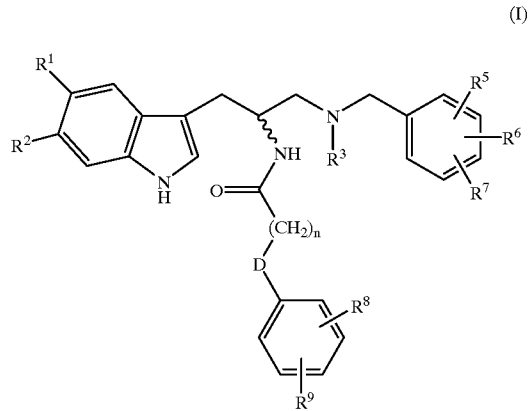

(I)

which are useful as tachykinin receptor antagonists. This invention also provides methods employing these compounds, as well as pharmaceutical formulations comprising these compounds.

4 Claims, No Drawings

2-ACYLAMINOPROPANAMINES AS TACHYKININ RECEPTOR ANTAGONISTS

This application is a 371 of PCT/US98/16333 filed Aug. 6, 1998.

BACKGROUND OF THE INVENTION

Tachykinins are a family of peptides which share a common amidated carboxy terminal sequence. Substance P was the first peptide of this family to be isolated, although its purification and the determination of its primary sequence did not occur until the early 1970's.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches. see. e.g., S. L. Shepheard, et al., *British Journal of Pharmacology*, 108:11–20 (1993); S. M. Moussaoui, et al., *European Journal of Pharmacology*, 238:421–424 (1993); and W. S. Lee, et al., *British Journal of Pharmacology*, 112:920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in U.S. Pat. No. 5,491,140, issued Feb. 13, 1996; U.S. Pat. No. 5,328,927, issued Jul. 12, 1994; U.S. Pat. No. 5,360,820, issued Nov. 1, 1994; U.S. Pat. No. 5,344,830, issued Sep. 6, 1994; U.S. Pat. No. 5,331,089, issued Jul. 19, 1994; European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993; Canadian Patent Application 2154116, published Jan. 23, 1996; European Patent Publication 693,489, published Jan. 24, 1996; and Canadian Patent Application 2151116, published Dec. 11, 1995.

U.S. Pat. No. 5,530,009, issued Jun. 25, 1996, describes a 1,2-diacylaminopropane for use in treating conditions associated with an excess of tachykinins. This patent also teaches processes for preparing this compound.

In essence, this invention provides a class of potent non-peptidyl tachykinin receptor antagonists similar to those of U.S. Pat. No. 5,530,009. By virtue of their non-peptidyl nature, the compounds of the present invention do not suffer from the shortcomings, in terms of metabolic instability, of known peptide-based tachykinin receptor antagonists.

SUMMARY OF THE INVENTION

This invention provides novel compounds of Formula I

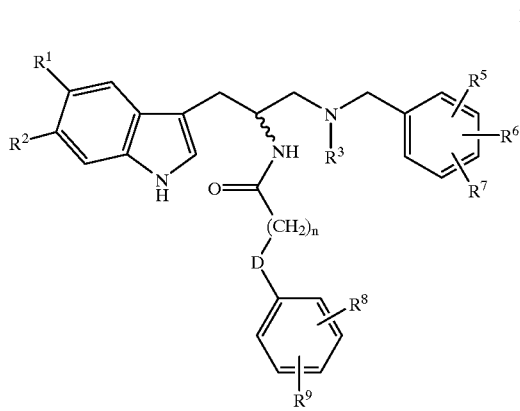

I wherein:
  $R^1$ and $R^2$ are independently hydrogen, halo, $C_1$–$C_6$ alkyl, hydroxy, or $C_1$–$C_6$ alkoxy;
  $R^5$, $R^6$, and $R^7$, are independently hydrogen, halo, $C_1$–$C_6$ alkyl, $C_1$–$C_6$ alkoxy, trifuoromethyl, or hydroxy;
  $R^3$ is hydrogen, $C_2$–$C_7$ alkanoyl, glycyl, or dimethyiglycyl;
  n is 1–6;
  D is —S(O)$_m$—, —NH—, —C(O)—, or —O—,
  m is 0, 1, or 2;
  $R^8$ and $R^9$ are independently hydrogen, hydroxy, $C_1$–$C_6$ alkyl, $C_1$–$C_6$ alkoxy, $C_1$–$C_6$ alkylthio, $C_1$–$C_6$ alkoxy ($C_1$–$C_6$ alkylenyl)-, $C_2$–$C_7$ alkoxycarbonyl, $C_2$–$C_7$ alkoxycarbonyl($C_1$–$C_6$ alkylenyl)-, trifluoromethoxy, trichloromethoxy, $C_1$–$C_6$ alkylthio, $C_1$–$C_6$ alkylamino, di($C_1$–$C_6$ alkyl)amino, formyl, cyano, halo, trifluoromethyl, $R^{10}R^{11}N(C_1$–$C_6$ alkylenyl)-, pyrrolyl, triazolyl, imidazolyl, tetrazolyl, thiazolyl, thiazolinyl, thiadiazolyl, thiadiazolinyl, piperidyl, pyrrolidyl, morpholinyl, morpholinocarbonyl, hexamethyleneiminyl, methylsulfonyl, methylsulfinyl, phenoxy, benzyloxy, carboxy, carbamoyl, or $C_2$–$C_7$ alkylcarbamoyl($C_1$–$C_6$ alkylenyl)-,
  $R^{10}$ and $R^{11}$ are independently hydrogen or $C_1$–$C_6$ alkyl,
  said $C_1$–$C_6$ alkyl or $C_1$–$C_6$ alkoxy groups being optionally substituted with one, two, or three moieties selected from the group consisting of hydroxy, halo, cyano, amino, nitro, carboxy, carbamoyl, and thiol;
  or $R^8$ and $R^9$ can combine, together with the benzo ring to which they are attached, to form a naphthyl, dihydronaphthyl, tetrahydronaphthyl, quinolinyl, isoquinolinyl, 2-coumaranonyl, 3-coumaranonyl, benzothiazolyl, benzimidazolyl, indolyl, benzothienyl, benzofuryl, 2,3-dihydrobenzofuryl, indolinyl, or 2,3-dihydrobenzothienyl group, which can be attached to D at any position of the bicyclic group;

or a pharmaceutically acceptable salt or solvate thereof.

In another embodiment this invention provides methods of treating a condition associated with an excess of tachykinins, which comprises administering to a mammal in need thereof an effective amount of a compound of Formula I, or a pharmaceutically acceptable salt or solvate thereof.

This invention also provides pharmaceutical formulations comprising, as an active ingredient, a compound of Formula I, or a pharmaceutically acceptable salt or solvate thereof, in combination with one or more pharmaceutically acceptable carriers, diluents, or excipients therefor.

DETAILED DESCRIPTION OF THE PREFERRED EMBODIMENTS

The terms and abbreviations used in the instant examples have their normal meanings unless otherwise designated. For example "° C." refers to degrees Celsius; "N" refers to normal or normality; "mol" refers to mole or moles; "mmol" refers to millimole or millimoles; "g" refers to gram or grams; "kg" refers to kilogram or kilograms; "L" refers to liter or liters; "ml" means milliliter or milliliters; "M" refers to molar or molarity; "MS" refers to mass spectrometry; and "NMR" refers to nuclear magnetic resonance spectroscopy.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the terms "$C_1$–$C_4$ alkoxy" and "$C_1$–$C_3$ alkoxy".

As used herein, the term "$C_1$–$C_{12}$ alkyl" refers to straight or branched, monovalent, saturated aliphatic chains of 1 to 12 carbon atoms and includes, but is not limited to, methyl, ethyl, propyl, isopropyl, butyl, isobutyl, t-butyl, pentyl, isopentyl, and hexyl. The term "$C_1$–$C_{12}$ alkyl" includes within its definition the terms "$C_1$–$C_6$ alkyl" and "$C_1$–$C_4$ alkyl".

"$C_2$–$C_7$ alkanoyloxy" represents a straight or branched alkyl chain having from one to six carbon atoms attached to a carbonyl moiety joined through an oxygen atom. Typical $C_2$–$C_7$ alkanoyloxy groups include acetoxy, propanoyloxy, isopropanoyloxy, butanoyloxy, t-butanoyloxy, pentanoyloxy, hexanoyloxy, 3-methylpentanoyloxy and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

"Halo" represents chloro, fluoro, bromo or iodo.

"$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio and the like.

"$C_1$–$C_{12}$ alkylenyl" refers to a straight or branched, divalent, saturated aliphatic chain of 1 to 12 carbon atoms and includes, but is not limited to, methylenyl, ethylenyl, propylenyl, isopropylenyl, butylenyl, isobutylenyl, t-butylenyl, pentylenyl, isopentylenyl, hexylenyl, octylenyl, 3-methyloctylenyl, decylenyl. The term "$C_1$–$C_6$ alkylenyl" is encompassed within the term "$C_1$–$C_{12}$ alkylenyl".

"$C_1$–$C_{10}$ alkylamino" represents a group of the formula

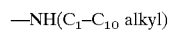
—NH($C_1$–$C_{10}$ alkyl)

wherein a chain having from one to ten carbon atoms is attached to an amino group. Typical $C_1$–$C_4$ alkylamino groups include methylamino, ethylamino, propylamino, isopropylamino, butylamino, sec-butylamino and the like.

"$C_2$–$C_6$ alkanoyl" represents a straight or branched alkyl chain having from one to five carbon atoms attached to a carbonyl moiety. Typical $C_2$–$C_6$ alkanoyl groups include ethanoyl (acetyl), propanoyl, isopropanoyl, butanoyl, t-butanoyl, pentanoyl, hexanoyl, 3-methylpentanoyl and the like.

"$C_2$–$C_7$ alkoxycarbonyl" represents a straight or branched alkoxy chain having from one to six carbon atoms attached to a carbonyl moiety. Typical $C_2$–$C_7$ alkoxycarbonyl groups include methoxycarbonyl, ethoxycarbonyl, propoxycarbonyl, isopropoxycarbonyl, butoxycarbonyl, t-butoxycarbonyl and the like.

The term "carbamoyl" as used herein refers to a moiety having one of the following structures.

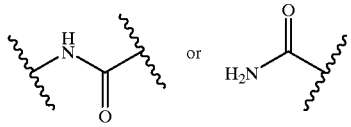

The term "$C_2$–$C_7$ alkylcarbamoyl" as used herein refers to a branched or unbranched chain of 1 to 6 carbon atoms combined with a carbamoyl group, as such is defined above. This moiety has the following structure.

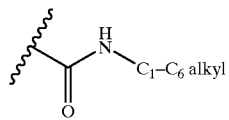

The term "haloformate" as used herein refers to an ester of a haloformic acid, this compound having the formula

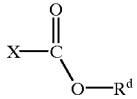

wherein X is halo, and $R^d$ is $C_1$–$C_6$ alkyl. Preferred haloformates are bromoformates and chloroformates. Especially preferred are chloroformates. Those haloformates wherein $R^d$ is $C_3$–$C_6$ alkyl are especially preferred. Most preferred is isobutylchloroformate.

The compounds prepared in the processes of the present invention have an asymmetric center. As a consequence of this chiral center, the compounds produced in the present invention may occur as racemates, mixtures of enantiomers and as individual enantiomers, as well as diastereomers and mixtures of diastereomers.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in Nomenclature of Organic Compounds: Principles and Practice, (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

The term "amino-protecting group" as used in the specification refers to substituents of the amino group commonly employed to block or protect the amino functionality while reacting other functional groups on the compound. Examples of such amino-protecting groups include formyl, trityl (herein abbreviated as "Tr"), phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl (herein abbreviated as "BoC"), 1,1-diphenyleth-1-yloxycarbonyl, 1,1-diphenylprop-1-yloxycarbonyl, 2-phenylprop-2-yloxycarbonyl, 2-p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, PROTECTIVE GROUPS IN ORGANIC SYNTHESIS, (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5, and T. W. Greene, et al., supra, at Chapter 5.

The term "hydroxy-protecting groups" as used herein refers to substituents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, $C_1$–$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl. Further examples of these groups may be found in T. W. Greene and P. G. M. Wuts, PROTECTIVE GROUPS IN ORGANIC SYNTHESIS, (1991) at Chapter 3.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

As noted supra, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formulas I. Many of the Formula I compounds can combine with solvents such as water, methanol, ethanol and acetonitrile to form pharmaceutically acceptable solvates such as the corresponding hydrate, methanolate, ethanolate and acetonitrilate.

This invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:
1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, DESIGN OF PRODRUGS, (1985).

The compounds of Formula I are generally prepared by reacting a compound of Formula II

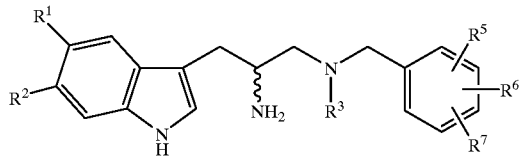

with an appropriately substituted carboxylic acid, anhydride, or carboxylic acid halide in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*. 34(48):7685 (1993)) and is very useful for the preparation of the compounds of the present invention. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired.

Another preferred method of preparing the compounds of Formula I where D is —O— is by reacting a compound of Formula III

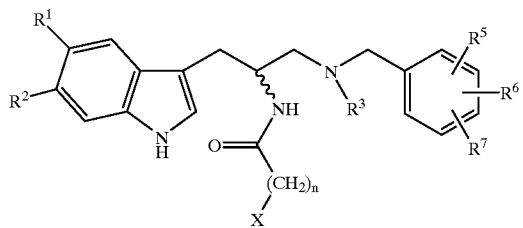

where X is a leaving group, preferably a halo moiety, most preferably a bromo group, with an appropriately substituted phenol, naphthol, or the like.

The most preferred method, to date, of synthesizing the intermediates of Formulae II and m is depicted in Scheme I, infra. Many of the steps of this synthesis are described in Patent Cooperation Treaty Publication WO 95/14017, published May 26, 1995; European Patent Application Publication 693,489, published Jan. 24, 1996; and U.S. Pat. No. 5,530,009, issued Jun. 25, 1996, the entire contents of which are herein incorporated by reference.

Scheme I

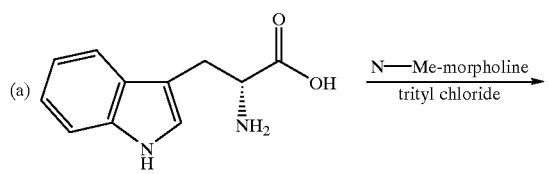

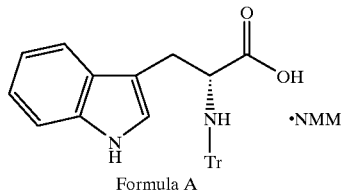
Formula A (b) 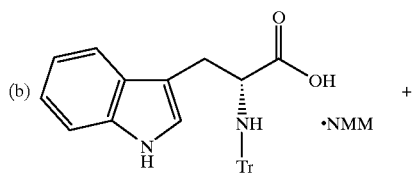

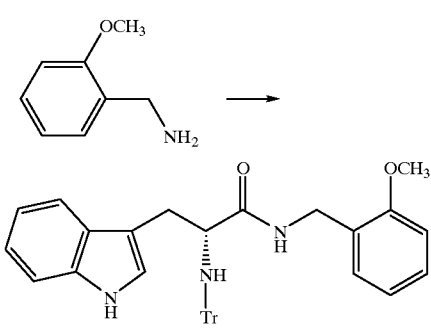

(c) 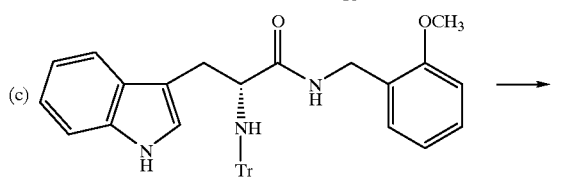

(d) 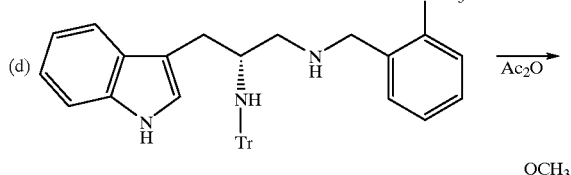 $\xrightarrow{Ac_2O}$

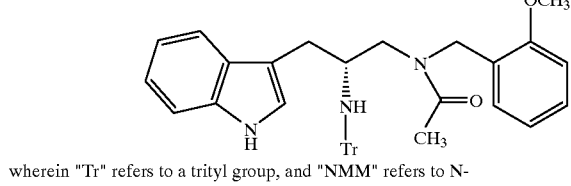

wherein "Tr" refers to a trityl group, and "NMM" refers to N-methylmorpholine.

(e) 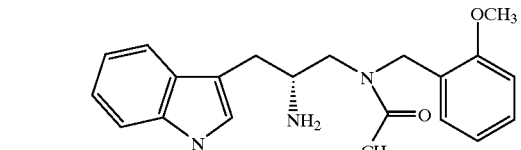

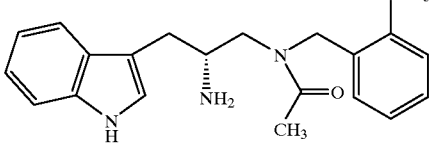

f) | bromoacetylation

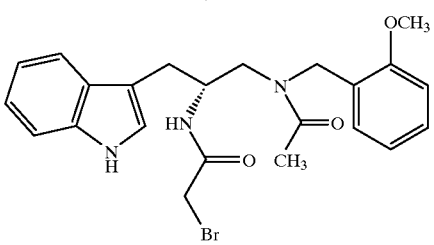

In another method of preparing the intermediates of Formulae II and m, Steps a) and b) can be combined as taught in U.S. patent application Ser. No. 60/021,849, filed Jul. 16, 1996. In this method a compound of the formula

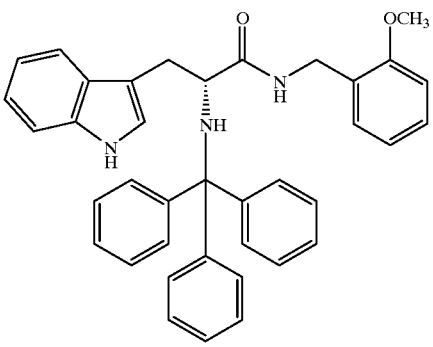

is prepared by reacting a compound of the formula

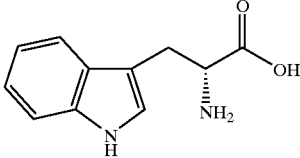

with bis(trimethylsilyl)amine in acetonitrile, followed by the addition of trityl chloride, N-methylmorpholine and 2-chloro-4,6-dimethoxy-1,3,5-triazine, in the presence of acetonitrile, and then adding 2-methoxybenzylamine.

The factor eventually found critical to the combination of the steps was the desilylation of the compound of Formula A, in Step (a), prior to ester formation via the addition of 2-chloro-4,6-dimethoxy-1,3,5-triazine (CDMT). In Step (a), desilylation had been accomplished by the addition of excess water prior to isolation which also dissolved any salts present. When desilylating Formula A in the combined chemistry, stoichiometry becomes increasingly important. Consideration must be given to the presence of excess HMDS used in the initial silylation of D-tryptophan. Simply adding a stoichiometric amount of methyl alcohol (or water) relative to D-tryptophan will not allow the subsequent esterification to progress. Methyl alcohol must also be added to quench all remaining unreacted HMDS. However, any excess methyl alcohol will consume CDMT and prevent complete esterification. Once the desilylation of the compound of Formula A and decomposition of excess HMDS is complete, the chemistry of Step (b) proceeds as expected and high quality desired intermediate is produced in good yield.

In the above process, the intermediate amides are reduced to amines using procedures well known in the art. These reductions can be performed using lithium aluminum hydride as well as by use of many other different aluminum-based hydrides. An especially preferred reagent employed in this reduction is RED-AL®, which is the tradename of a 3.4 M solution of sodium bis(2-methoxyethoxy)aluminum hydride in toluene. Alternatively, the amides can be reduced by catalytic hydrogenation, though high temperatures and pressures are usually required for this. Sodium borohydride in combination with other reagents may be used to reduce the amide. Borane complexes, such as a borane dimethyl-sulfide complex, are especially useful in this reduction reaction.

The acylation of the secondary amine can be done using any of a large number of techniques regularly employed by those skilled in organic chemistry. One such reaction scheme is a substitution using an anhydride such as acetic anhydride. Another reaction scheme often employed to acylate a secondary amine employs a carboxylic acid preferably with an activating agent. An amino-de-alkoxylation type of reaction uses esters as a means of acylating the amine. Activated esters which are attenuated to provide enhanced selectivity are very efficient acylating agents. One preferred such activated ester is p-nitrophenyl ester, such as p-nitrophenyl acetate.

Primary amines can also be acylated using amides to perform what is essentially an exchange reaction. This reaction is usually carried out with the salt of the amine. Boron trifluoride, usually in the form of a boron trifluoride diethyl ether complex, is frequently added to this reaction to complex with the leaving ammonia.

An additional step is one of substitution of the secondary amine. For most of the compounds of Formula I this substitution is one of alkylation, acylation, or sulfonation. This substitution is usually accomplished using well recognized means. Typically, alkylations can be achieved using alkyl halides and the like as well as the well-known reductive alkylation methods, employing aldehydes or ketones. Many of the acylating reaction protocols discussed supra efficiently acylate the secondary amine as well. Alkyl- and aryl-sulfonyl chlorides can be employed to sulfonate the secondary amine.

In many instances one of the later steps in the synthesis of the compounds of Formulae II and Im is the removal of an amino- or carboxy-protecting group. Such procedures, which vary, depending upon the type of protecting group employed as well as the relative lability of other moieties on the compound, are described in detail in many standard references works such as T. W. Greene, et al., PROTECTIVE GROUPS IN ORGANIC SYNTHESIS (1991).

The following Examples and Preparations further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use.

Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz. (Unless designated otherwise, the term "NMR" as employed herein refers to proton nuclear magnetic resonance.) Free atom bombardment mass spectroscopy (FAB) was performed on a VG ZAB-2SE instrument. Field desorption mass spectroscopy (FDMS) was performed using either a VG 70SE or a Varian MAT 731 instrument.

Optical rotations were measured with a Perkin-Elmer 241 polarimeter. Chromatographic separation on a Waters Prep 500 LC was generally carried out using a linear gradient of the solvents indicated in the text unless otherwise specified.

The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 ml of 10% aqueous sulfuric acid] and then heated on a hot plate). Preparative centrifugal thin layer chromatography was performed on a Harrison Model 7924A Chromatotron using Analtech silica gel GF rotors.

Cation exchange chromatography was performed with Dowex® 50X8-100 ion exchange resin. Anion exchange chromatography was performed with Bio-Rad AG® 1-X8 anion-exchange resin (acetate form converted to hydroxide form). Flash chromatography was performed as described by Still, et al., *Journal of Organic Chemistry*, 43:2923 (1978).

Optical rotations are reported at the sodium-D-line (354 nm). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Thomas Hoover capillary melting point apparatus or a Buchi melting point apparatus, and are uncorrected.

The following methods provide illustrative protocols for preparing the compounds of Formula I as depicted in the Schemes supra. Throughout the Methods and Examples, infra, the terms "NMR", "IR", and "UV" indicate that the proton nuclear magnetic resonance, infrared, and ultraviolet spectroscopy, respectively, were consistent with the desired title product.

Preparation 1
Preparation of (R)-3-(1H-indol-3-yl)-N-(2-methoxybenzyl)-2-(N-triphenylmethylamino)propanamide.

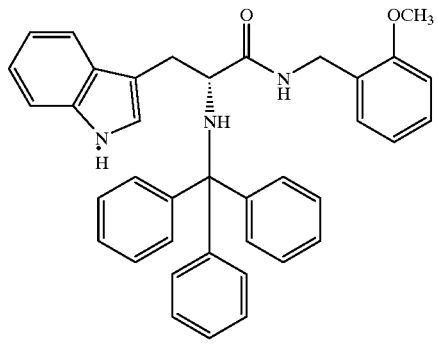

In a 50 gallon, glass-lined reactor, L-tryptophan (4.50 kg, 22.0 mol) was added to acetonitrile (30 L, 6.7 vol) at 20° C. This reactor was vented to a scrubber containing water, intended to scrub ammonia generated during the silylation reaction and HCl generated during the tritylation and esterification reactions. Bis(trimethylsilyl)amine (HMDS, 5.81 L, 27.5 mol, 1.25 eq) was transferred by gravity to the L-tryptophan slurry from a plastic carboy. The carboy was rinsed with acetonitrile (0.5 L). The slurry was heated to 55° C. and stirred until reaction completion. The reaction endpoint was defined as the point at which the slurry has completely gone into solution. The reaction was clear yellow at completion and took about 2 hours.

Trityl chloride (6.45 kg, 23.1 mol, 1.05 eq) was slurried in acetonitrile (30 L, 6.7 vol) and transferred into the reactor at 47° C., using trapped vacuum at 325 mm Hg.

N-methylmorpholine (5.38 L, 48.9 mol, 2.20 eq) was also transferred into the reactor at this time. The reaction slurry was heated and maintained at 55° C. until reaction completion, determined by high performance liquid chromatography analysis. Reaction time was about 2.5 hours.

The reactor was isolated from the scrubber, and cooled to 35–40° C. Methyl alcohol (2.29 L, 56.5 mol, 2.55 eq.) was charged to the reactor and the mixture cooled to 25° C. 2-Chloro-4,6-dimethoxy-1,3,5-triazine (CDMT, 4.14 kg, 23.61 mol, 1.07 eq) was added to the reactor with acetonitrile (28 L, 6.2 vol) at 25° C. The reactor was again vented to the scrubber. The reaction slurry was stirred at room temperature until completion. The reaction endpoint is determined by high performance liquid chromatography analysis. Reaction time is approximately 2 hours. The reactor was isolated from the scrubber following the reaction.

2-Methoxybenzylamine (3.11 L, 23.8 mol, 1.08 eq) was charged to the reactor from a plastic carboy by gravity. The slurry thickens with the addition of 2-methoxybenzylamine. The reaction slurry was heated to 35° C. and stirred until reaction completion, determined by high performance liquid chromatography analysis. Reaction time was 2.5 hours.

Water (45 kg, 10 vol) was pre-weighed into a separate 50 gallon, glass-lined tank. The water was pressure-transferred into the reaction mixture slurry over about 45 minutes. The resulting yellow-colored slurry was cooled to 0–5° C. over two hours and stirred overnight.

The title intermediate was isolated by vertical basket centrifuge isolation using three micron polyethylene multiple filament isolation bag. During the centrifugation, the load speed was generally between 900–1050 rpm, the wash speed was 900–1500 rpm, and the spin speed was 1500–2300 rpm.

The title intermediate was then dried by rotary vacuum drying. Yield: 86.4% with isomer purity of 99.6%.

Preparation 2
Reduction of Carbonyl

Preparation of (R)-3-(1H-indol-3-yl)-1-[N-(2-methoxybenzyl)amino]-2-N-triphenylmethylamino)propane

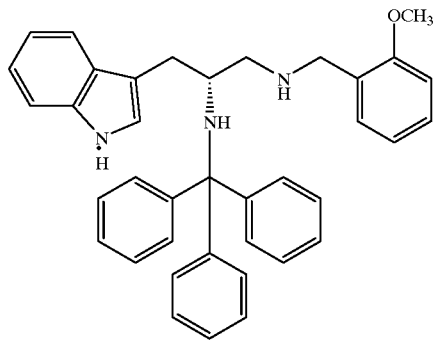

RED-AL®, [a 3.4 M, solution of sodium bis(2-methoxyethoxy)aluminum hydride in toluene] (535 ml, 1.819 mol), dissolved in anhydrous tetrahydrofuran (400 ml) was slowly added using an addition funnel to a refluxing solution of the acylation product, (R)-3-(1H-indol-3-yl)-N-(2-methoxybenzyl)-2-(N-triphenylmethylamino)propanamide (228.6 g, 0.404 mol) produced supra, in anhydrous tetrahydrofuran (1.0 L) under a nitrogen atmosphere. The reaction mixture became a purple solution. The reaction was quenched after at least 20 hours by the slow addition of excess saturated Rochelle's salt solution (potassium sodium tartrate tetrahydrate). The organic layer was isolated, washed with brine (2×), dried over anhydrous sodium sulfate, filtered, and concentrated to an oil on a rotary evaporator. No further purification was done and the product was used directly in the next step.

Preparation 3
Acylation of Secondary Amine

Preparation of (R)-3-(1H-indol-3-yl)-1-[N-(2-methoxybenzyl)-acetylamino]-2-(N-triphenylmethylamino)propane

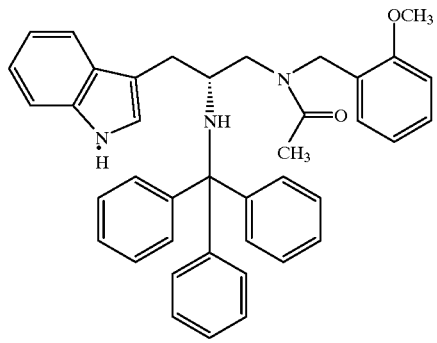

To a stirring solution of (R)-3-(1H-indol-3-yl)-1-[N-(2-methoxybenzyl)amino]-2-(N-triphenylmethylamino)propane (0.404 mol) in anhydrous tetrahydrofuran (1.2 L) under a nitrogen atmosphere at 0° C. was added triethylamine (66.5 ml, 0.477 mol) and acetic anhydride (45.0 ml, 0.477 mol). After 4 hours, the mixture was concentrated on a rotary evaporator, redissolved in methylene chloride and ethyl acetate, washed with water (2x) and brine (2x), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of (R)-3-(1H-indol-3-yl)-1-[N-(2-methoxybenzyl) acetylamino]-2-(N-triphenylmethylamino)propane was crystallized and isolated over three crops giving 208.97 grams (87% yield) of analytically pure material. Analysis for $C_{40}H_{39}N_3O_2$:

Theory: C, 80.91; H, 6.62; N, 7.08.

Found: C, 81.00; H, 6.69; N, 6.94.

Preparation 4

Deprotection

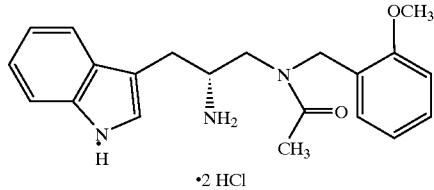

•2 HCl

Preparation of (R)-2-amino-3-(1H-indol-3-yl)-1-[N-(2-methoxybenzyl)acetylaminolpropane dihydrochloride A stirring solution of (R)-3-(1H-indol-3-yl)-1-[N-(2-methoxybenzyl)acetylamino]-2-(N-triphenylmethylamino) propane in two volumes of methylene chloride was cooled to between –40° C. and –50° C. Anhydrous hydrogen chloride gas was added at such a rate that the temperature of the reaction mixture did not exceed 0° C. The reaction mixture was stirred for 30 minutes to one hour at 0–10° C.

To this reaction mixture was added two volumes of methyl t-butyl ether and the resulting mixture was allowed to stir for 30 minutes to one hour at 0–10° C. The resulting crystalline solid was removed by filtration and then washed with methyl t-butyl ether. The reaction product was dried under vacuum at 50° C. (Yield>98%) Analysis for $C_{21}H_{25}N_3O_2 \cdot 2$ HCl:

Theory: C, 59.44; H, 6.41; N, 9.90.

Found: C, 60.40; H, 6.60; N, 9.99.

Preparation 5

Preparation of (R)-2-[(2-bromo)acetyl]amino-3-(1H-indol-3-yl)-1-[N-(2-methoxybenzyl)acetylamino] propane

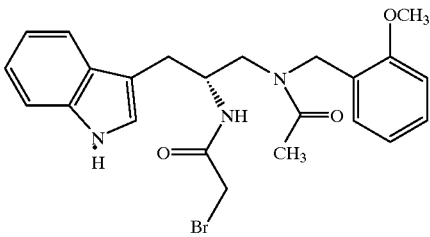

To a stirring solution of (R)-2-amino-3-(1H-indol-3-yl)-1-[N-(2-methoxybenzyl)acetylamino]propane (7.51 g, 21.369 mmol) in anhydrous tetrahydrofuran (100 ml) under a nitrogen atmosphere at 0° C. were added diisopropylethylamine (4.1 ml, 23.537 mmol) and bromoacetyl bromide (2.05 ml, 23.530 mmol). After 2 hours, ethyl acetate was added and the reaction mixture washed with water twice, 1.0 N hydrochloric acid (2x), saturated sodium bicarbonate solution (2x), and brine. The organic layer was dried over anhydrous sodium sulfate, filtered, and concentrated to a tan foam on a rotary evaporator. In this manner the 2-[(2-bromo) acetyl]amino-3-(1H-indol-3-yl)-1-[N-(2-methoxybenzyl) acetylamino]propane was obtained in quantitative yield. No further purification was necessary.

Preparation 6

Preparation of a polystyrene bound isocyanate resin

To a stirred suspension of 50 grams (61 mmol) aminomethylated polystyrene resin (1.22 mmol/g) in 800 ml toluene was added 193 ml (366 mmol) 1.9 M phosgene in toluene. After stirring the reaction mixture for 10 minutes, 67 ml (482 mmol) triethylamine was added and the reaction mixture was stirred for 18 hours at room temperature. The mixture was filtered and the recovered solid washed with 10 times with dichloromethane. A light pink resin mixed with a white solid was obtained. This solid mixture was resuspended in 700 ml dichloromethane, stirred for 10 minutes and then filtered and washed well with dichloromethane. The resulting solid was again suspended, stirred and washed with dichloromethane to provide the desired resin. IR(KBr): 2252 $cm^{-1}$ (characteristic peak for —N═C═O)

General Procedure I

To a suspension of three equivalents of polymer-bound 1-piperidine in 1 ml of chloroform (R)-2-amino-3-(1H-indol-3-yl)-1-[N-(2-methoxybenzyl)acetylamino]propane dihydrochloride (10 mg, 0.024 mmol, 1 eq) was dissolved. To this mixture was added the appropriate carboxylic acid (0.036 mmol, 1.5 eq) and polymer-bound 1-(3-dimethylaminopropyl)-3-propylcarbodiimide hydrochloride (108 mg, 0.108 mmol, 4.5 eq). The resulting mixture was agitated at ambient temperature for about 2–3 days. Unreacted (R)-2-amino-3-(1H-indol-3-yl)-1-[N-(2-methoxybenzyl)acetylamino]propane dihydrochloride was removed by the addition of an excess of polystyrene bound isocyanate resin and rocked for four hours. The reaction mixtures were filtered and the filtrates were concentrated.

General Procedure II

In a reaction vial potassium tert-butoxide (19.38 mg, 0.158 mmol, 3 eq) and an appropriate substituted phenol or naphthol (0.158 mmol, 3 eq) were admixed in 0.7 ml of dry tetrahydrofuran. To this mixture (R)-2-[(2-bromo)acetyl]amino-3-(1H-indol-3-yl)-1-[N-(2-methoxybenzyl)acetylamino]propane (25 mg, 0.053 mmol, 1 eq) was added and the resulting mixture was heated for two hours at 80° C. The solvents were removed in vacuo and the residue was redissolved in methylene chloride and washed once with water. The organic fraction was dried over sodium sulfate. The solvents were removed in vacuo.

EXAMPLE 1

Preparation of (R)-2-[(2-phenoxy)acetyl]amino-3-(1H-indol-3-yl)-1-[N-(2-methoxybenzyl)acetylamino]propane

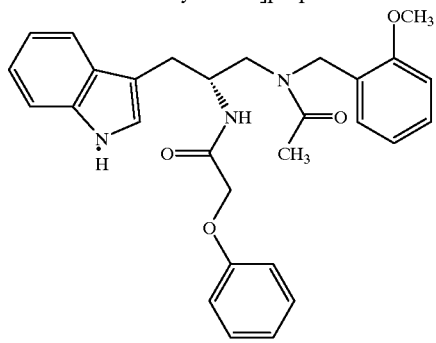

NMR was consistent with the proposed title structure.

EXAMPLE 2

Preparation of (R)-2-[[2-(4-methoxymethyl)phenoxy]acetyl]amino-3-(1H-indol-3-yl)-1-[N-(2-methoxybenzyl)acetylamino]propane

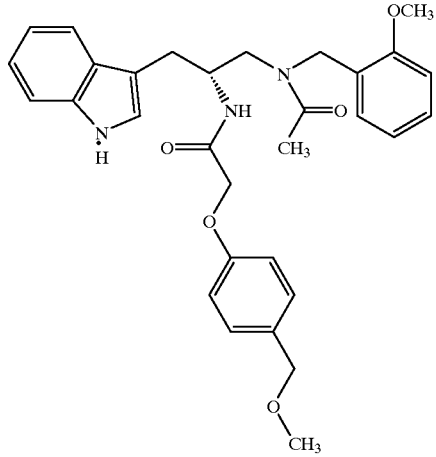

NMR was consistent with the proposed title structure.

EXAMPLE 3

Preparation of (R)-2-[[2-(4-carboxy)phenoxy]acetyl]amino-3-(1H-indol-3-yl)-1-[N-(2-methoxybenzyl)acetylamino]propane

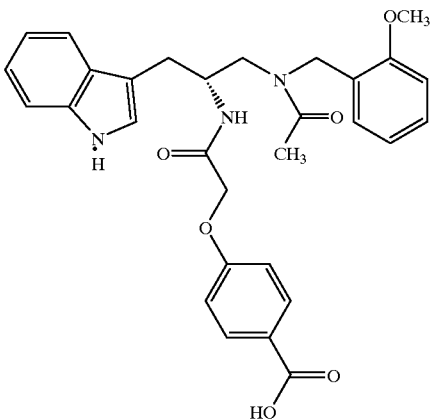

NMR was consistent with the proposed title structure.

EXAMPLE 4

Preparation of (R)-2-[[2-(4-ethoxy)phenoxy]acetyl]amino-3-(1H-indol-3-yl)-1-[N-(2-methoxybenzyl)acetylamino]propane

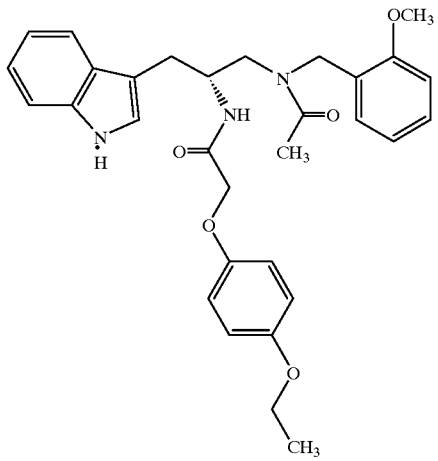

NMR was consistent with the proposed title structure.

EXAMPLE 5

Preparation of (R)-2-[[2-(4-methoxycarbonyl)phenoxy]acetyl]amino-3-(1H-indol-3-yl)-1-[N-(2-methoxybenzyl)acetylamino]propane

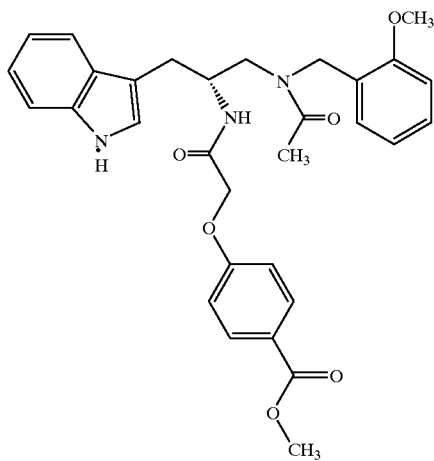

NMR was consistent with the proposed title structure.

EXAMPLE 6

Preparation of (R)-2-[[2-(4-trifluoromethoxy)phenoxy]acetyl]amino-3-(1H-indol-3-yl)-1-[N-(2-methoxybenzyl)acetylamino]propane

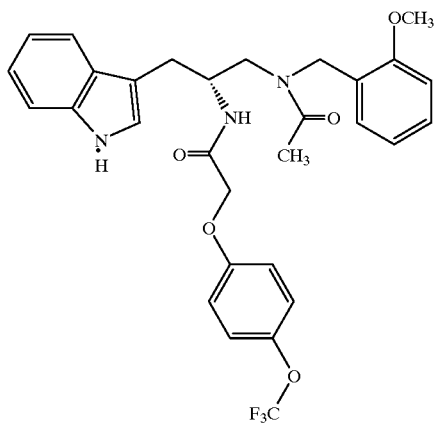

NMR was consistent with the proposed title structure.

EXAMPLE 7

Preparation of (R)-2-[[2-[4-[[(methoxy)carbonyl]methyl]]phenoxy]acetyl]-amino-3-(1H-indol-3-yl)-1-[N-(2-methoxybenzyl)acetylamino]propane

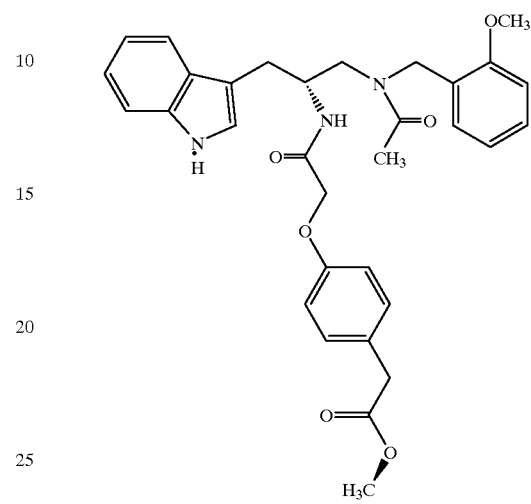

NMR was consistent with the proposed title structure.

EXAMPLE 8

Preparation of (R)-2-[[2-[4-[[(methoxy)carbonyl]ethyl]]phenoxy]acetyl]-amino-3-(1H-indol-3-yl)-1-[N-(2-methoxybenzyl)acetylamino]propane

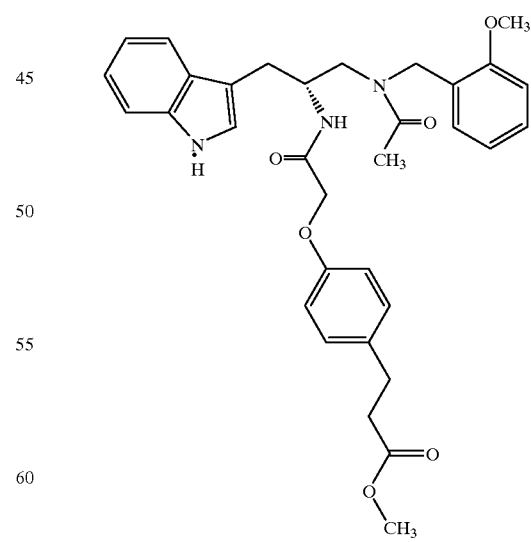

NMR was consistent with the proposed title structure.

EXAMPLE 9

Preparation of (R)-2-[2-(naphth-2-yloxy)acetyl]amino-3-(1H-indol-3-yl)-1-[N-(2-methoxybenzyl)acetylamino]propane

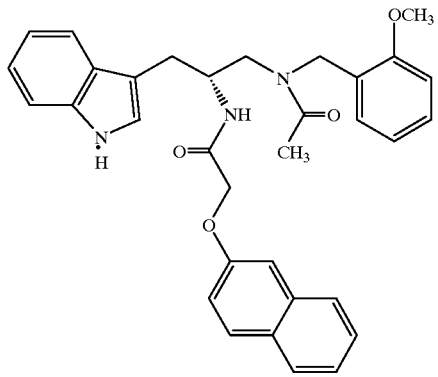

NMR was consistent with the proposed title structure.

EXAMPLE 10

Preparation of (R)-2-[2-(4-acetylphenoxy)acetyl]-amino-3-(1H-indol-3-yl)-1-[N-(2-methoxybenzyl)acetylamino]propane

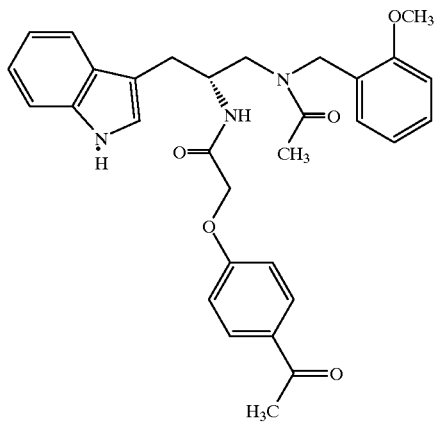

NMR was consistent with the proposed title structure.

EXAMPLE 11

Preparation of (R)-2-[2-(4-hydroxyphenoxy)acetyl]-amino-3-(1H-indol-3-yl)-1-[N-(2-methoxybenzyl)acetylamino]propane

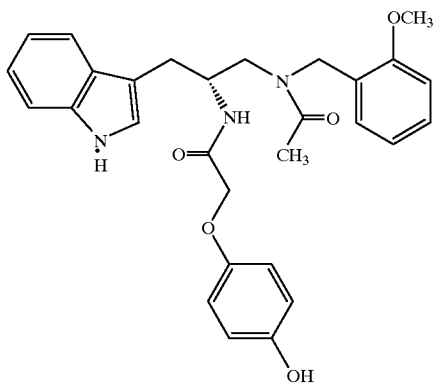

NMR was consistent with the proposed title structure.

EXAMPLE 12

Preparation of (R)-2-[2-(4-chlorophenoxy)acetyl]-amino-3-(1H-indol-3-yl)-1-[N-(2-methoxybenzyl)acetylamino]propane

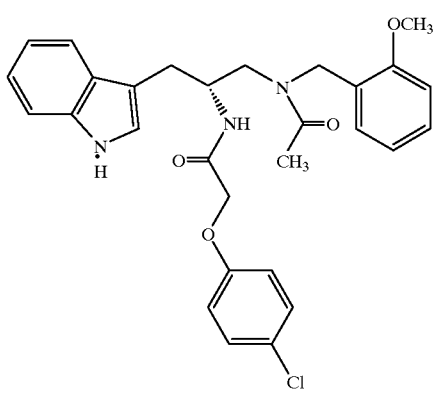

NMR was consistent with the proposed title structure.

EXAMPLE 13

Preparation of (R)-2-[2-[4-(benzyloxy)phenoxy]acetyl]-amino-3-(1H-indol-3-yl)-1-[N-(2-methoxybenzyl)acetylamino]propane

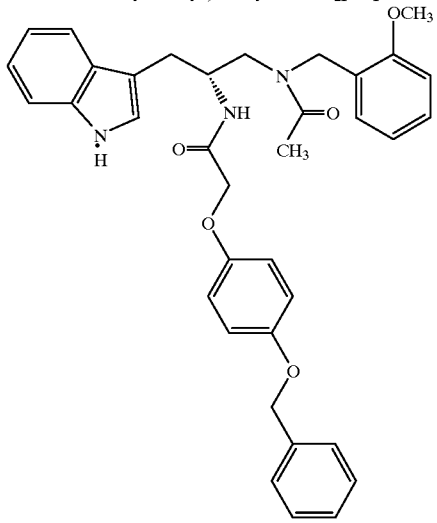

NMR was consistent with the proposed title structure.

EXAMPLE 14

Preparation of (R)-2-[2-(4-hydroxymethylphenoxy) acetyl]-amino-3-(1H-indol-3-yl)-1-[N-(2-methoxybenzyl)acetylamino]propane

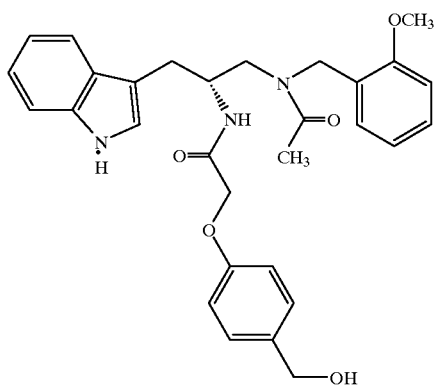

NMR was consistent with the proposed title structure.

EXAMPLE 15

Preparation of (R)-2-[2-(4-methoxyphenoxy)acetyl]-amino-3-(1H-indol-3-yl)-1-[N-(2-methoxybenzyl) acetylamino]propane

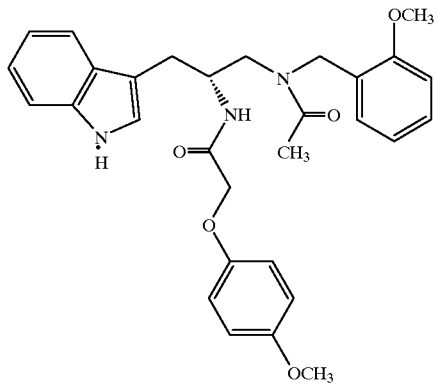

NMR was consistent with the proposed title structure.

EXAMPLE 16

Preparation of (R)-2-[2-(3-methoxyphenoxy)acetyl]-amino-3-(1H-indol-3-yl)-1-[N-(2-methoxybenzyl) acetylamino]propane

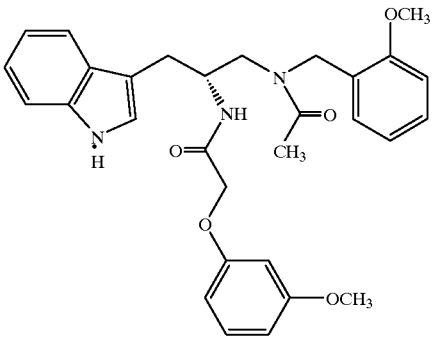

NMR was consistent with the proposed title structure.

EXAMPLE 17

Preparation of (R)-2-[2-(2-methoxyphenoxy)acetyl]-amino-3-(1H-indol-3-yl)-1-[N-(2-methoxybenzyl) acetylamino]propane

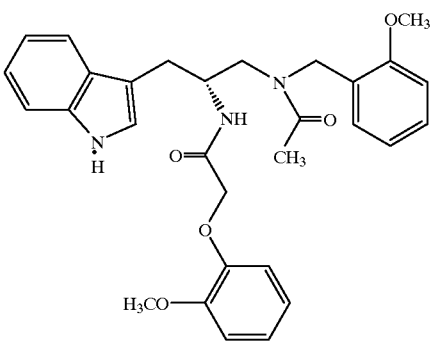

NMR was consistent with the proposed title structure.

EXAMPLE 18

Preparation of (R)-2-[2-(2-chlorophenoxy)acetyl]-amino-3-(1H-indol-3-yl)-1-[N-(2-methoxybenzyl) acetylamino]propane

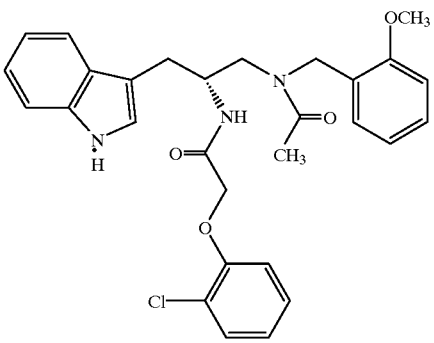

NMR was consistent with the proposed title structure.

EXAMPLE 19

Preparation of (R)-2-[2-(2-carbamoylphenoxy)acetyl]-amino-3-(1H-indol-3-yl)-1-[N-(2-methoxybenzyl)acetylamino]propane

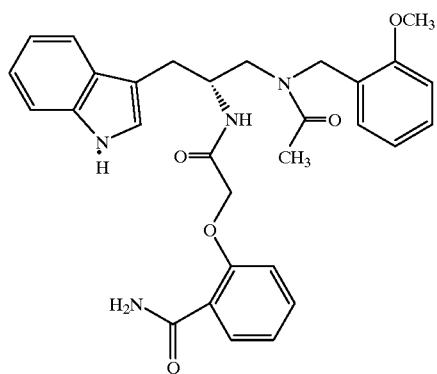

NMR was consistent with the proposed title structure.

EXAMPLE 20

Preparation of (R)-2-[2-(3,4-dichlorophenoxy)acetyl]-amino-3-(1H-indol-3-yl)-1-[N-(2-methoxybenzyl)acetylamino]propane

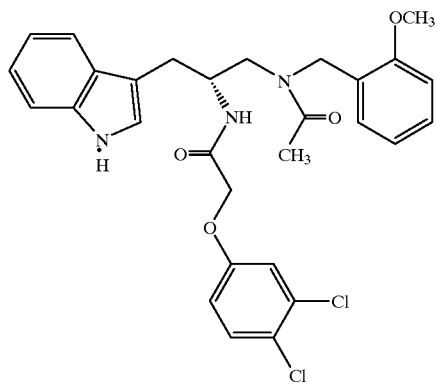

NMR was consistent with the proposed title structure.

EXAMPLE 21

Preparation of (R)-2-[2-(4-fluorophenoxy)acetyl]-amino-3-(1H-indol-3-yl)-1-[N-(2-methoxybenzyl)acetylamino]propane

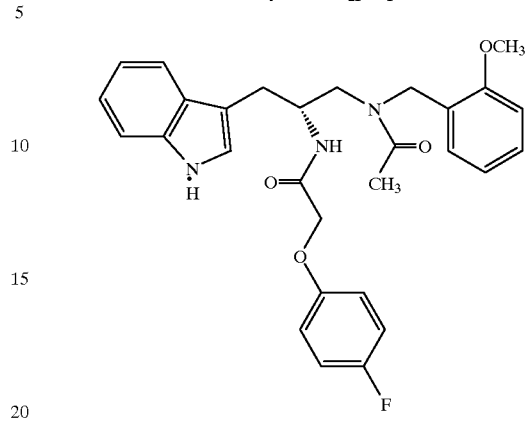

NMR was consistent with the proposed title structure.

EXAMPLE 22

Preparation of (R)-2-[2-(4-nitrophenoxy)acetyl]-amino-3-(1H-indol-3-yl)-1-[N-(2-methoxybenzyl)acetylamino]propane

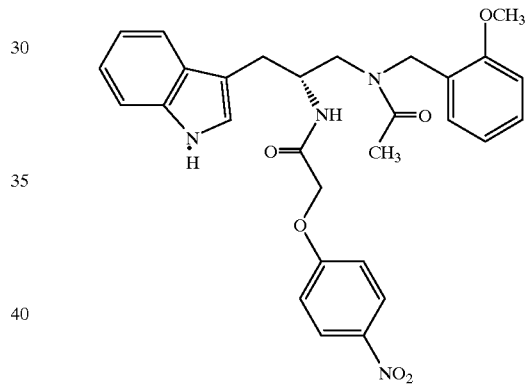

NMR was consistent with the proposed title structure.

EXAMPLE 23

Preparation of (R)-2-[2-[4-(2-hydroxyethyl)phenoxy]acetyl]-amino-3-(1H-indol-3-yl)-1-[N-(2-methoxybenzyl)acetylamino]propane

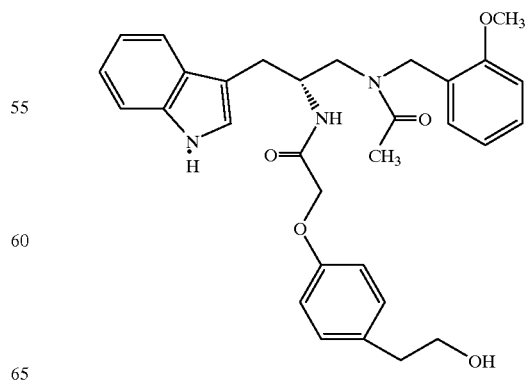

NMR was consistent with the proposed title structure.

EXAMPLE 24

Preparation of 2-[2-[4-(3-hydroxypropyl)phenoxy]acetyl]-amino-3-(1H-indol-3-yl)-1-[N-(2-methoxybenzyl)acetylamino]propane

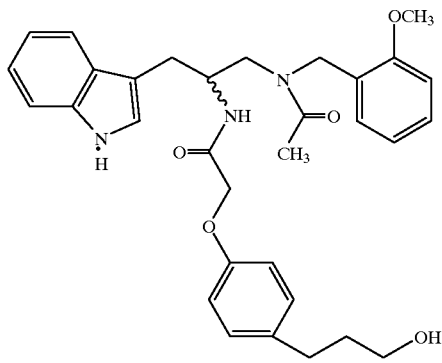

NMR was consistent with the proposed title structure.

EXAMPLE 25

Preparation of 2-[2-[4-(2-carbamoylethyl)phenoxy]acetyl]-amino-3-(1H-indol-3-yl)-1-[N-(2-methoxybenzyl)acetylamino]propane

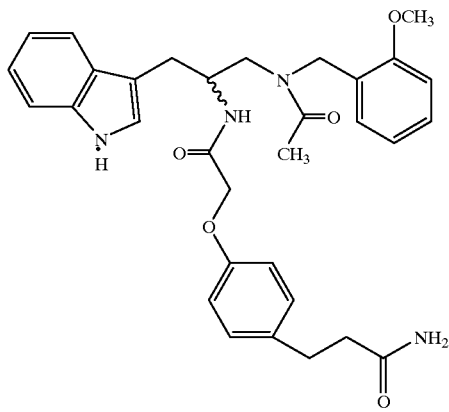

NMR was consistent with the proposed title structure.

EXAMPLE 26

Preparation of 2-[2-[4-(triazol-1-yl)phenoxy]acetyl]-amino-3-(1H-indol-3-yl)-1-[N-(2-methoxybenzyl)acetylamino]propane

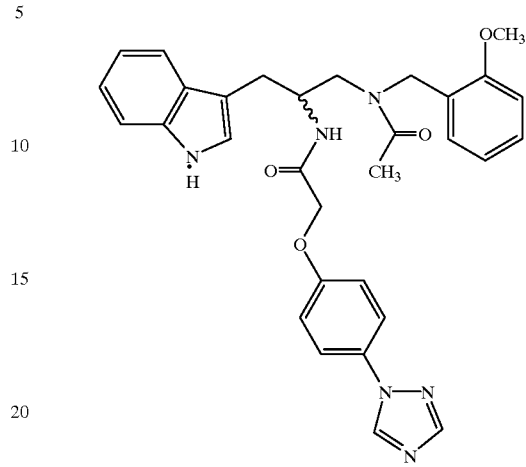

NMR was consistent with the proposed title structure.

EXAMPLE 27

Preparation of 2-[2-[4-(ethyl)phenoxy]acetyl]-amino-3-(1H-indol-3-yl)-1-[N-(2-methoxybenzyl)acetylamino]propane

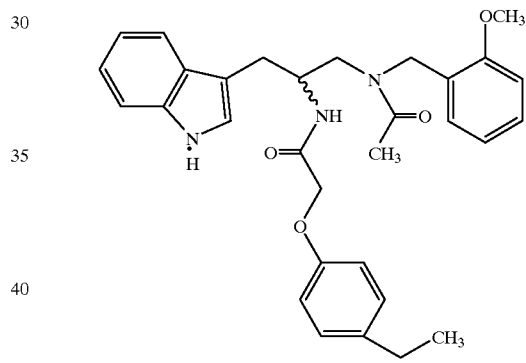

NMR was consistent with the proposed title structure.

EXAMPLE 28

Preparation of 2-[2-[4-(n-propyl)phenoxy]acetyl]-amino-3-(1H-indol-3-yl)-1-[N-(2-methoxybenzyl)acetylamino]propane

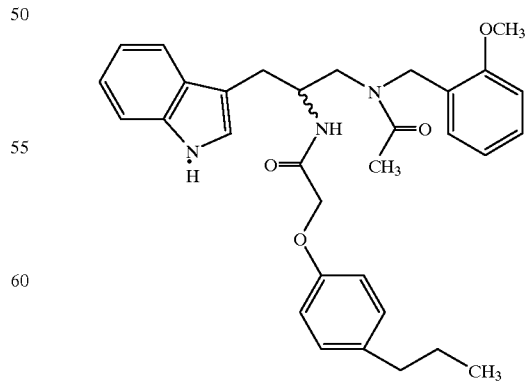

NMR was consistent with the proposed title structure.

EXAMPLE 29

Preparation of 2-[2-[2-(hydroxymethyl)phenoxy]acetyl]-amino-3-(1H-indol-3-yl)-1-[N-(2-methoxybenzyl)acetylamino]propane

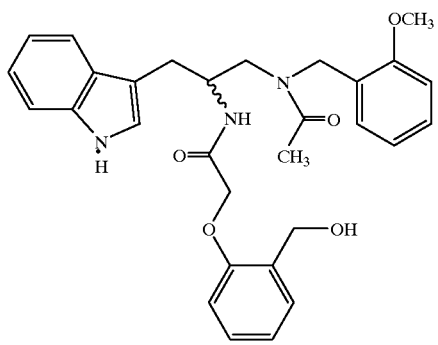

NMR was consistent with the proposed title structure.

EXAMPLE 30

Preparation of 2-[2-[4-(2-methoxyethyl)phenoxy]acetyl]-amino-3-(1H-indol-3-yl)-1-[N-(2-methoxybenzyl)acetylamino]propane

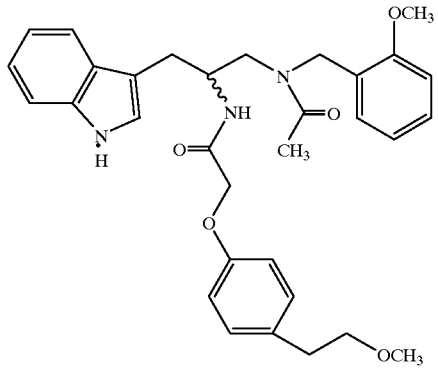

NMR was consistent with the proposed title structure.

EXAMPLE 31

Preparation of 2-[2-[4-[(morpholin-4-yl)carbonyl]phenoxy]acetyl]-amino-3-(1H-indol-3-yl)-1-[N-(2-methoxybenzyl)acetylamino]propane

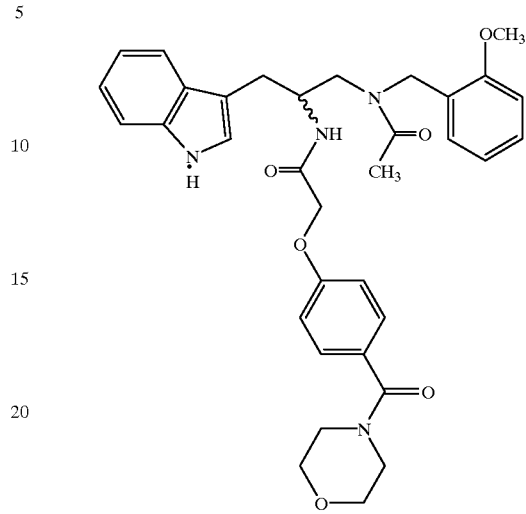

NMR was consistent with the proposed title structure.

EXAMPLE 32

Preparation of 2-[2-[4-(4-hydroxybutyl)phenoxy]acetyl]-amino-3-(1H-indol-3-yl)-1-[N-(2-methoxybenzyl)acetylamino]propane

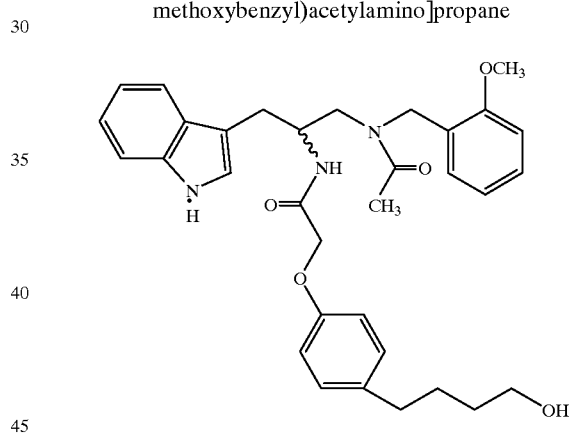

NMR was consistent with the proposed title structure.

EXAMPLE 33

Preparation of 2-[2-[2-coumaranon-5-yl-oxy]acetyl]-amino-3-(1H-indol-3-yl)-1-[N-(2-methoxybenzyl)acetylamino]propane

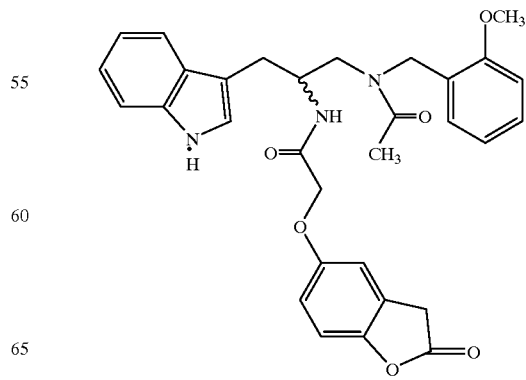

NMR was consistent with the proposed title structure.

EXAMPLE 34

Preparation of 2-[2-[benzothiazol-6-yl-oxy]acetyl]-amino-3-(1H-indol-3-yl)-1-[N-(2-methoxybenzyl)acetylamino]propane

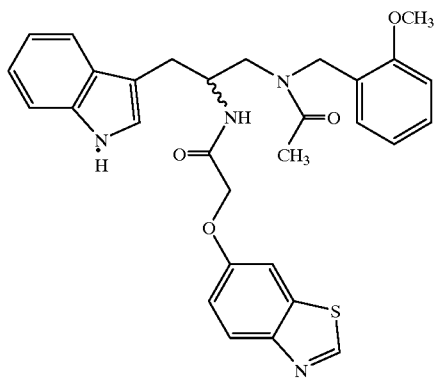

NMR was consistent with the proposed title structure.

EXAMPLE 35

Preparation of 2-[2-[4-(methylsulfonyl)phenoxy]acetyl]-amino-3-(1H-indol-3-yl)-1-[N-(2-methoxybenzyl)acetylamino]propane

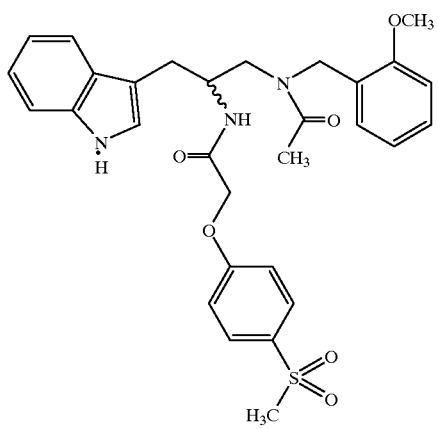

NMR was consistent with the proposed title structure.

EXAMPLE 35

Preparation of 2-[2-[4-(methylsulfonyl)phenoxy]acetyl]-amino-3-(1H-indol-3-yl)-1-[N-(2-methoxybenzyl)acetylamino]propane

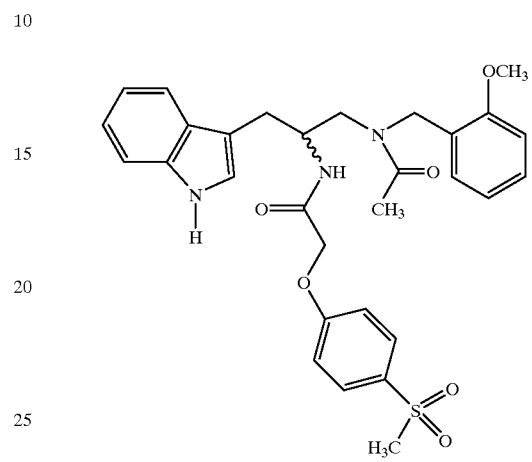

NMR was consistent with the proposed title structure.

EXAMPLE 36

Preparation of 2-[2-[quinolin-6-yl]acetyl]-amino-3-(1H-indol-3-yl)-1-[N-(2-methoxybenzyl)acetylamino]propane

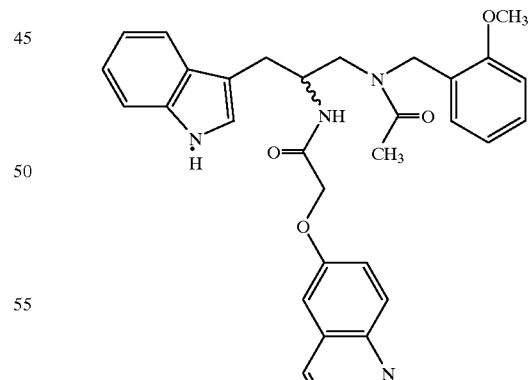

NMR was consistent with the proposed title structure.

EXAMPLE 37

Preparation of 2-[2-[4-(3-cyanopropyl)phenoxy]acetyl]-amino-3-(1H-indol-3-yl)-1-[N-(2-methoxybenzyl)acetylamino]propane

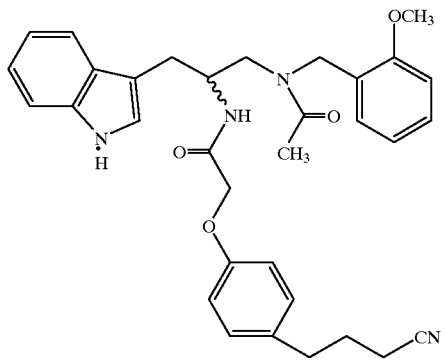

NMR was consistent with the proposed title structure.

EXAMPLE 38

Preparation of 2-[2-[4-(imidazol-1-yl)phenoxy]acetyl]-amino-3-(1H-indol-3-yl)-1-[N-(2-methoxybenzyl)acetylamino]propane

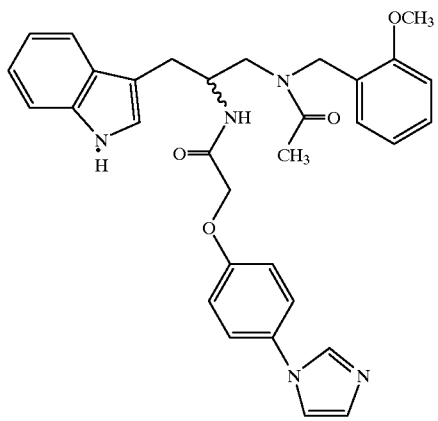

NMR was consistent with the proposed title structure.

EXAMPLE 39

Preparation of 2-[2-[4-(cyanomethyl)phenoxy]acetyl]-amino-3-(1H-indol-3-yl)-1-[N-(2-methoxybenzyl)acetylamino]propane

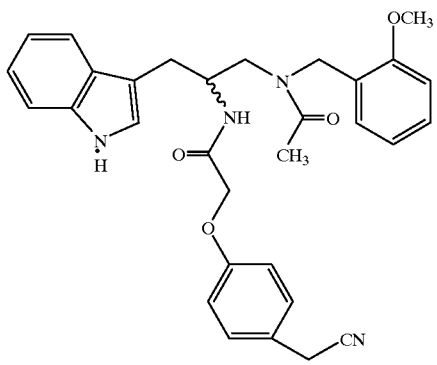

NMR was consistent with the proposed title structure.

EXAMPLE 40

Preparation of 2-[2-[4-(isopropyl)phenoxy]acetyl]-amino-3-(1H-indol-3-yl)-1-[N-(2-methoxybenzyl)acetylamino]propane

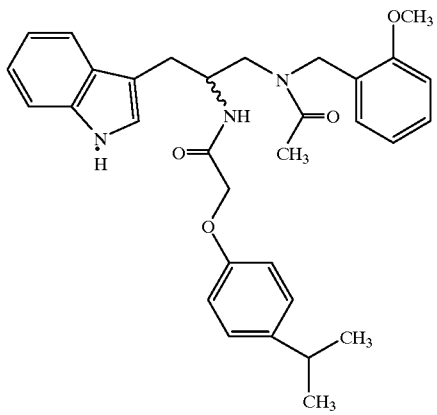

NMR was consistent with the proposed title structure.

EXAMPLE 41

Preparation of 2-[2-[3-(hydroxymethyl)phenoxy]acetyl]-amino-3-(1H-indol-3-yl)-1-[N-(2-methoxybenzyl)acetylamino]propane

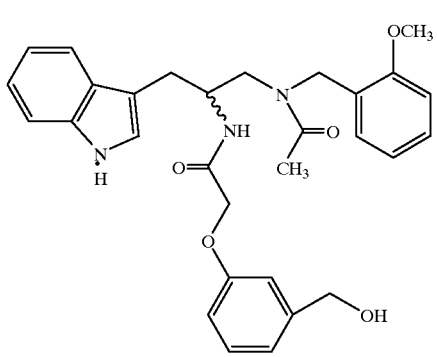

NMR was consistent with the proposed title structure.

EXAMPLE 42

Preparation of 2-[2-[4-[[(methylamino)carbonyl]methyl]phenoxy]acetyl]-amino-3-(1H-indol-3-yl)-1-[N-(2-methoxybenzyl)acetylamino]propane

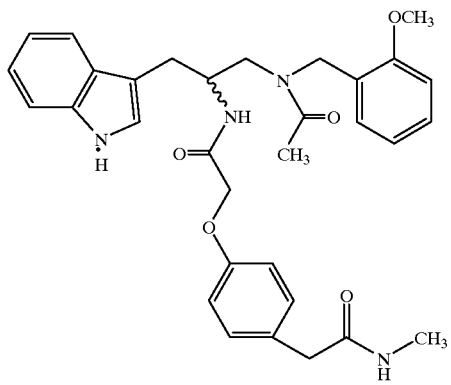

NMR was consistent with the proposed title structure.

EXAMPLE 43

Preparation of 2-[2-[4-(formyl)phenoxy]acetyl]-amino-3-(1H-indol-3-yl)-1-[N-(2-methoxybenzyl)acetylamino]propane

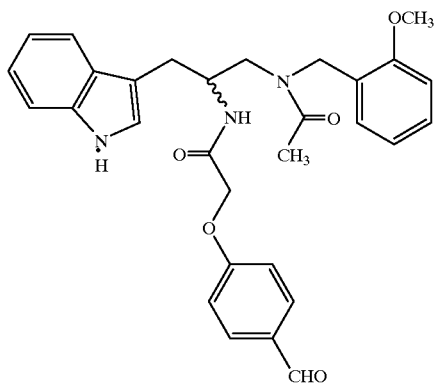

NMR was consistent with the proposed title structure.

EXAMPLE 44

Preparation of 2-[2-[4-(thiazolin-2-yl)phenoxy]acetyl]-amino-3-(1H-indol-3-yl)-1-[N-(2-methoxybenzyl)acetylamino]propane

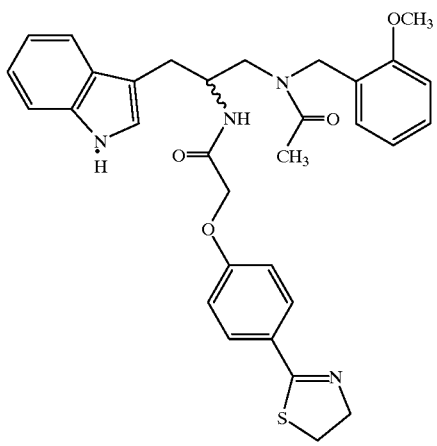

NMR was consistent with the proposed title structure.

EXAMPLE 45

Preparation of 2-[2-[4-(cyano)phenoxy]acetyl]-amino-3-(1H-indol-3-yl)-1-[N-(2-methoxybenzyl)acetylamino]propane

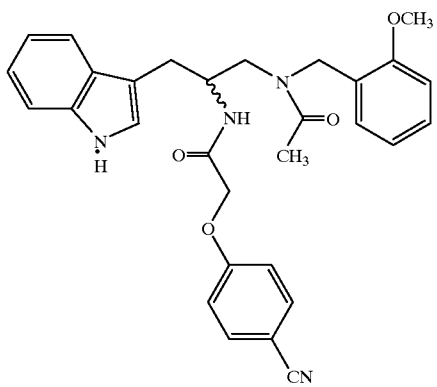

NMR was consistent with the proposed title structure.

EXAMPLE 46

Preparation of 2-[2-[4-(3-methyl-2-pyrazolin-5-yl)phenoxy]acetyl]-amino-3-(1H-indol-3-yl)-1-[N-(2-methoxybenzyl)acetylamino]propane

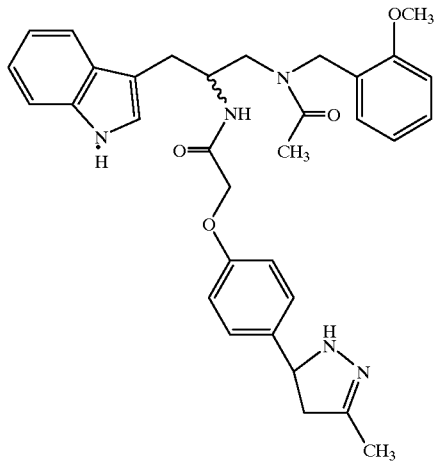

NMR was consistent with the proposed title structure.

EXAMPLE 47

Preparation of 2-[2-[4-[2-(acetyl)ethyl]phenoxy]acetyl]-amino-3-(1H-indol-3-yl)-1-[N-(2-methoxybenzyl)acetylamino]propane

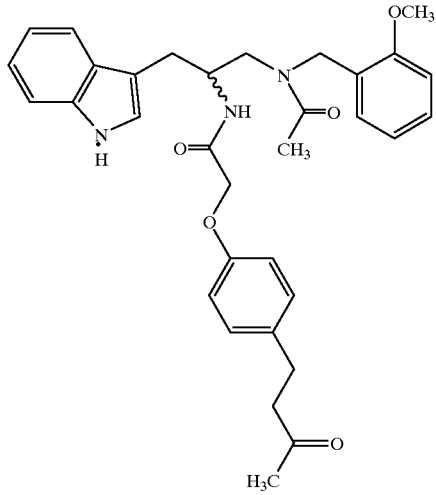

NMR was consistent with the proposed title structure

EXAMPLE 48

Preparation of 2-[2-[3-(2-hydroxyethyl)phenoxy]acetyl]-amino-3-(1H-indol-3-yl)-1-[N-(2-methoxybenzyl)acetylamino]propane

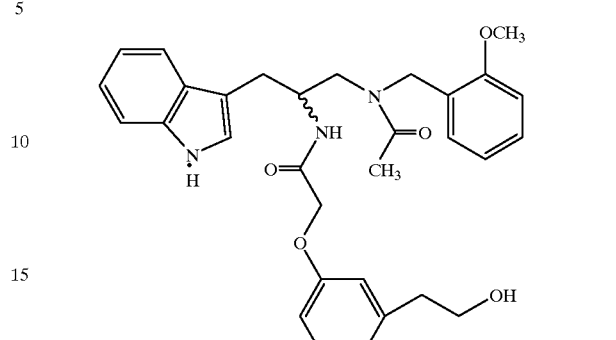

NMR was consistent with the proposed title structure.

EXAMPLE 49

Preparation of 2-[2-[4-[[(butylamino)carbonyl]amino]phenoxy]acetyl]-amino-3-(1H-indol-3-yl)-1-[N-(2-methoxybenzyl)acetylamino]propane

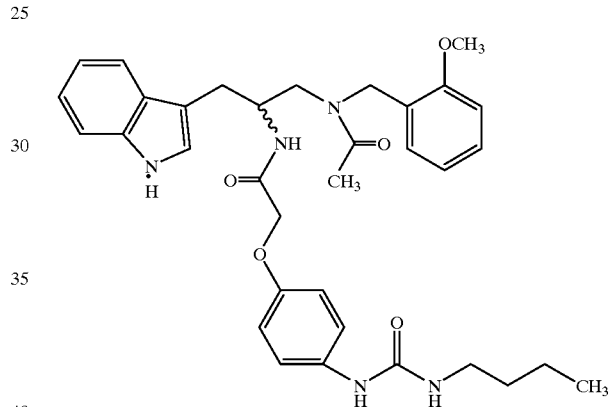

NMR was consistent with the proposed title structure.

EXAMPLE 50

Preparation of 2-[2-[4-(3,5-dichlorophenoxy)phenoxy]acetyl]-amino-3-(1H-indol-3-yl)-1-[N-(2-methoxybenzyl)acetylamino]propane

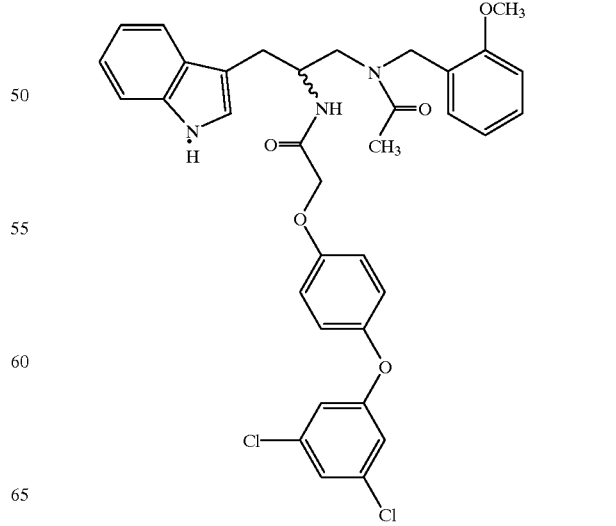

NMR was consistent with the proposed title structure.

EXAMPLE 51

Preparation of 2-[2-[4-(acetamido)phenoxy]acetyl]-amino-3-(1H-indol-3-yl)-1-[N-(2-methoxybenzyl)acetylamino]propane

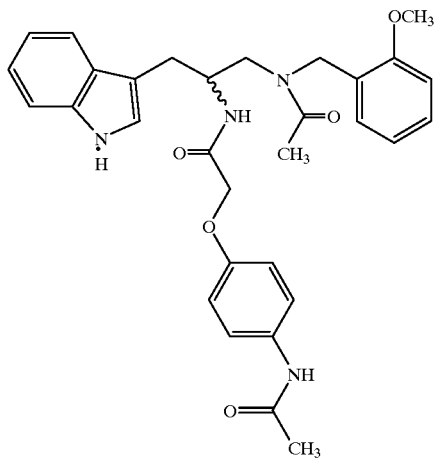

NMR was consistent with the proposed title structure.

EXAMPLE 52

Preparation of 2-[2-[4-(acetoxy)phenoxy]acetyl]-amino-3-(1H-indol-3-yl)-1-[N-(2-methoxybenzyl)acetylamino]propane

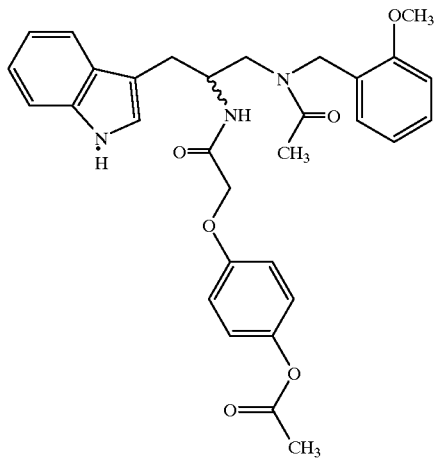

NMR was consistent with the proposed title structure.

EXAMPLE 53

Preparation of 2-[3-phenylsulfonyl)propanoyl]amino-3-(1H-indol-3-yl)-1-[N-(2-methoxybenzyl)acetylamino]propane

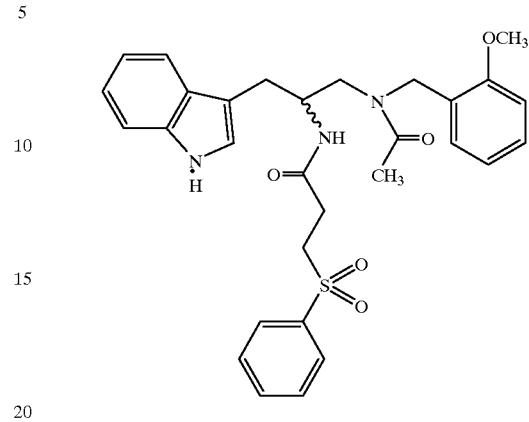

NMR was consistent with the proposed title structure.

EXAMPLE 54

Preparation of 2-[4-(2,4-dichlorophenoxy)butanoyl]amino-3-(1H-indol-3-yl)-1-[N-(2-methoxybenzyl)acetylamino]propane

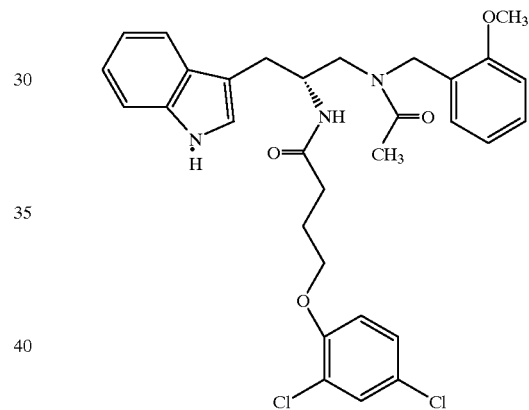

NMR was consistent with the proposed title structure.

EXAMPLE 55

Preparation of 2-[3-[benzothiazol-2-ylthio]propanoyl]-amino-3-(1H-indol-3-yl)-1-[N-(2-methoxybenzyl)acetylamino]propane

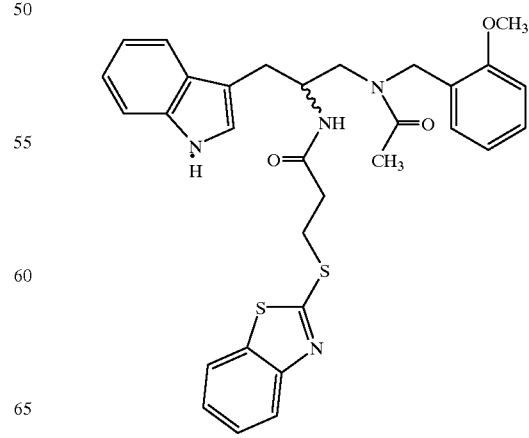

NMR was consistent with the proposed title structure.

EXAMPLE 56

Preparation of 2-[2-[4-(imidazol-1-yl)phenoxy]acetyl]-amino-3-(1H-indol-3-yl)-1-[N-(2-methoxybenzyl)acetylamino]propane

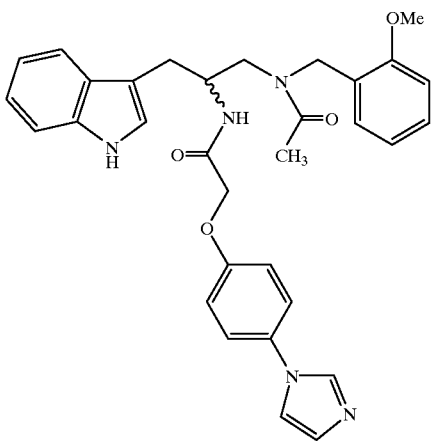

NMR was consistent with the proposed title structure.

EXAMPLE 57

Preparation of 2-[2-[4-(imidazol-1-yl)phenoxy]acetyl]-amino-3-(1H-indol-3-yl)-1-[N-(2-chlorobenzyl)acetylamino]propane

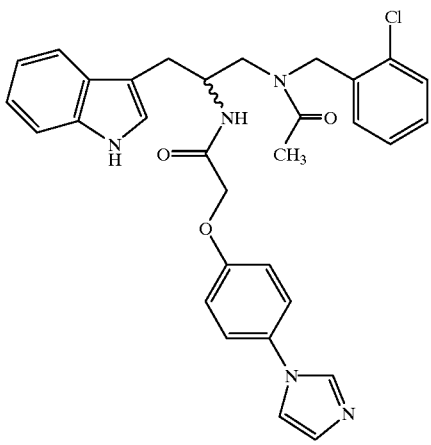

NMR was consistent with the proposed title structure.

EXAMPLE 57A

Preparation of 2-[2-[4-(1,2,3-thiadiazol-4-yl)phenoxy]acetyl]-amino-3-(1H-indol-3-yl)-1-[N-(2-methoxybenzyl)acetylamino]propane

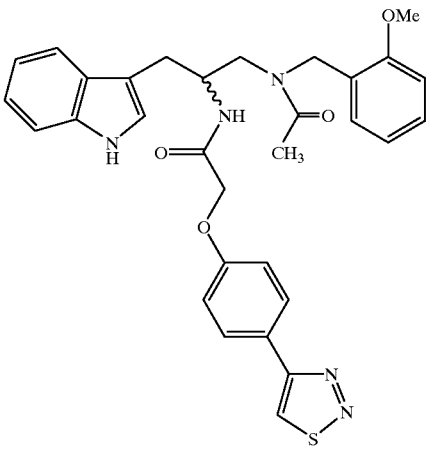

NMR was consistent with the proposed title structure. MS-FD 569 (M+).

EXAMPLE 58

Preparation of 2-[3-[benzoyl]ethanoyl]-amino-3-(1H-indol-3-yl)-1-[N-(2-methoxybenzyl)acetylamino]propane

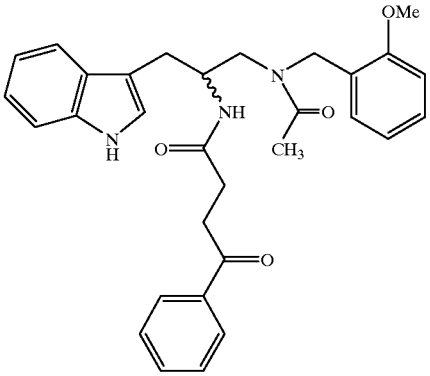

NMR was consistent with the proposed title structure. MS-FD 569 (M+).

The compounds of the present invention possess tachykinin receptor activity. The biological efficacy of a compound believed to be effective as a tachykinin receptor antagonist may be confirmed by employing an initial screening assay which rapidly and accurately measured the binding of the tested compound to known NK-1 and NK-2 receptor sites. Assays useful for evaluating tachykinin receptor antagonists are well known in the art. See, e.g., J. Jukic, et al., *Life Sciences*, 49:1463–1469 (1991); N. Kucharczyk, et al., *Journal of Medicinal Chemistry*, 36:1654–1661 (1993); N. Rouissi, et al., *Biochemical and Biophysical Research Communications*, 176:894–901 (1991).

NK-1 Receptor Binding Assay

Radioreceptor binding assays were performed using a derivative of a previously published protocol. D. G. Payan, et al., *Journal of Immunology*, 133:3260–3265 (1984). In this assay an aliquot of IM9 cells (1×10$^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See. e.g., *Annals of the New York Academy of Science*, 190: 221–234 (1972); *Nature (London)*, 251:443–444 (1974); *Proceedings of the National Academy of Sciences (USA)*, 71:84–88 (1974). These cells were routinely cultured in RPMI 1640 supplemented with 50 μg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, were grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000 ×g) for 30 minutes using a Beckman JA-14® rotor. The pellets were washed once using the above procedure. and the final pellets were resuspended in 100–120 ml 50 mM Tris buffer, pH 7.4, and 4 ml aliquots stored frozen at −70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 μg/ml chymostatin. A 200 μl volume of the homogenate (40 μg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 μl; the final concentration in the assay was 20 pM. Non-specific binding was determined using 1 μM eledoisin. Ten concentrations of eledoisin from 0.1 to 1000 nM were used for a standard concentration-response curve.

All samples and standards were added to the incubation in 10 μl dimethylsulfoxide (DMSO) for screening (single dose) or in 5 μl DMSO for IC$_{50}$ determinations. The order of additions for incubation was 190 or 195 μl assay buffer, 200 μl homogenate, 10 or 5 μl sample in DMSO, 100 μl radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 ml of cold 50 mM Tris buffer, pH 7.7. The filter circles were then punched into 12×75 mm polystyrene tubes and counted in a gamma counter.

Animal and human clinical models demonstrating the effectiveness of the methods of the present invention are well known to those skilled in the art. For example, the following experiment clearly demonstrates the inhibitory effect of the compounds of the present invention on an animal model predictive of migraine therapies.

Neurogenic Plasma Estravasation in the Dural Layer Induced by Electrical Stimulation Harlan Sprague-Dawley rats (225–325 g) or guinea pigs from Charles River Laboratories (225–325 g) are anesthetized with sodium phenobarbitol (65 mg/kg or 45 mg/kg, respectively, intraperitoneally) and placed in a stereotaxic frame (David Kopf Instruments) with the incisor bar set at −3.5 mm for rats or −4.0 mm for guinea pigs. Following a midline sagital scalp incision, two pairs of bilateral holes are drilled through the skull (6 mm posteriorly, 2.0 and 4.0 mm laterally for rats; 4 mm posteriorly and 3.2 and 5.2 mm laterally for guinea pigs—all coordinates reference to bregma). Pairs of stainless steel stimulating electrodes, insulated except for the tips, are lowered through the holes in both hemispheres to a depth of 9 mm (rats) or 10.5 mm (guinea pigs) from dura.

The femoral vein is exposed and a dose of the test compound is injected intravenously (1 ml/kg). Approximately seven minutes later, a 50 mg/kg dose of Evans Blue, a fluorescent dye, is also injected intravenously. The Evans Blue complexed with proteins in the blood and functioned as a marker for protein extravasation. Exactly ten minutes post-injection of the test compound, the left trigeminal ganglion is stimulated for three minutes at a current intensity of 1.0 mA (5 Hz, 4 msec duration) with a potentiostat/galvanostat.

Fifteen minutes following the stimulation, the animals are killed and exanguinated with 20 ml of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope equipped with a grating monochromator and a spectrophotometer is used to quantify the amount of Evans Blue dye in each tissue sample. An excitation wavelength of approximately 535 nm is utilized and the emission intensity at 600 nm is determined. The microscope is equipped with a motorized stage and is interfaced with a personal computer. This facilitated the computer-controlled movement of the stage with fluorescence measurements at 25 points (500 μm steps) on each dural sample. The mean and standard deviation of the measurements are determined by the computer.

The dural extravasation induced by electrical stimulation of the trigeminal ganglion is an ipsilateral effect (i.e. it occurs only on the side of the dura in which the trigeminal ganglion is stimulated). This allowed the other, unstimulated, half of the dura to be used as a control. The ratio of the amount of extravasation in the dura from the stimulated side compared to the unstimulated side is calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve is generated and the dose that inhibited the extravasation by 50% ($ID_{50}$) is estimated.

The compounds prepared by the processes of the present invention are useful as tachykinin receptor-binding compounds. As such, they may be employed as antagonists or agonists of the various tachykinins. These compounds are, therefore, useful in the treatment or prevention of conditions associated with an excess or deficiency of tachykinins. The term "physiological disorder associated with an excess or deficiency of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease and irritable bowel syndrome; disorders of bladder function such as bladder detrusor hyper-reflexia and incontinence; atherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Reynaud's disease; emesis; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as inflammatory bowel disease, osteoarthritis and rheumatoid arthritis; adverse immunological disorders such as rejection of transplanted tissues; gastrointestinal disorders and diseases such as disorders associated with the neuronal control of viscera such as ulcerative colitis, Crohn's disease and irritable bowel syndrome; incontinence; disorders of blood flow caused by vasodilation; and pain or nociception, for example, that attributable to or associated with any of the foregoing conditions or the transmission of pain in migraine.

The results of several experiments demonstrate that many of the compounds of Formula I are selective tachykinin receptor antagonists. These compounds preferentially bind one tachykinin receptor subtype compared to other such receptors. Such compounds are especially preferred.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, sunburn pain, neuropathic pain, opioid-resistant pain, visceral pain, surgical pain, bone injury pain, pain during labor and delivery, pain resulting from burns, post partum pain, angina pain, and genitourinary tract-related pain including cystitis.

In addition to pain, NK-1 antagonists are especially preferred in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; atherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

In addition to the in vitro binding assays described supra, many of the compounds prepared by the processes of the present invention have also been tested in in vivo model systems for conditions associated with an excess of tachykinins. Of those compounds tested in vivo many have shown efficacy against said conditions.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See. e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
|---|---|
| Active Ingredient | 250.0 mg |
| Isotonic saline | 1000 ml |

Formulation Preparation 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
|---|---|
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C.

When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound, and the state of the patient.

We claim:

1. A compound of the formula

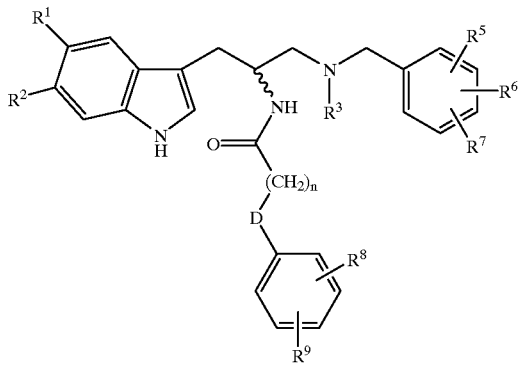

wherein:

$R^1$ and $R^2$ are independently hydrogen, halo, $C_1$–$C_6$ alkyl, hydroxy, or $C_1$–$C_6$ alkoxy;

$R^5$, $R^6$, and $R^7$, are independently hydrogen, halo, $C_1$–$C_6$ alkyl, $C_1$–$C_6$ alkoxy, trifluoromethyl, or hydroxy;

$R^3$ is hydrogen, $C_2$–$C_7$ alkanoyl, glycyl, or dimethylglycyl;

n is 1–6;

D is —S(O)$_m$—, —NH—, —C(O)—, or —O—, m is 0, 1, or 2;

$R^8$ and $R^9$ are independently hydrogen, hydroxy, substituted $C_1$–$C_6$ alkyl, substituted $C_1$–$C_6$ alkoxy, $C_1$–$C_6$ alkylthio, $C_2$–$C_7$ alkoxycarbonyl($C_1$–$C_6$ alkylenyl)-, $C_2$–$C_7$ alkanoyloxy, trifluoromethoxy, trichloromethoxy, $C_1$–$C_6$ alkylthio, formyl, cyano, $R^{10}R^{11}N(C_1$–$C_6$ alkylenyl)-, pyrrolyl, pyrazolinyl, triazolyl, imidazolyl, tetrazolyl, thiazolyl, thiazolinyl, thiadiazolyl, thiadiazolinyl, piperidyl, pyrrolidyl, morpholinyl, morpholinocarbonyl, hexamethyleneiminyl, methylsulfonyl, methylsulfinyl, phenoxy, benzyloxy, carboxy, carbamoyl, or $C_2$–$C_7$ alkylcarbamoyl($C_1$–$C_6$ alkylenyl)-, $R^{10}$ and $R^{11}$ are independently hydrogen or $C_1$–$C_6$ alkyl, said substituted $C_1$–$C_6$ alkyl or substituted $C_1$–$C_6$ alkoxy groups being substituted with one, two, or three moieties selected from the group consisting of hydroxy, acetyl, oxo, halo, cyano, amino, nitro, carboxy, carbamoyl, and thiol;

or $R^8$ and $R^9$ can combine, together with the benzo ring to which they are attached, to form a naphthyl, dihydronaphthyl, tetrahydronaphthyl, quinolinyl, isoquinolinyl, 2-coumaranonyl, 3-coumaranonyl, benzothiazolyl, benzimidazolyl, indolyl, benzothienyl, benzofuryl, 2,3-dihydrobenzofuryl, indolinyl, or 2,3-dihydrobenzothienyl group, which can be attached to D at any position of the bicyclic group;

with the proviso that when D is —O— or when m=0, $R^8$ and $R^9$ cannot both be hydrogen;

or a pharmaceutically acceptable salt or solvate thereof.

2. A compound selected from the group consisting of (R)-2-[2-(4-hydroxymethylphenoxy)acetyl]-amino-3-(1H-indol-3-yl)-1-[N-(2-methoxybenzyl)acetylamino]propane, (R)-2-[2-(2-carbamoylphenoxy)acetyl]-amino-3-(1H-indol-3-yl)-1-[N-(2-methoxybenzyl)acetylamino]propane, 2-[2-[4-(triazol-1-yl)phenoxy]acetyl]-amino-3-(1H-indol-3-yl)-1-[N-(2-methoxybenzyl)acetylamino]propane, 2-[2-[quinolin-6-yl]acetyl]-amino-3-(1H-indol-3-yl)-1-[N-(2-methoxybenzyl)acetylamino]propane, 2-[2-[4-(imidazol-1-yl)phenoxy]acetyl]-amino-3-(1H-indol-3-yl)-1-[N-(2-methoxybenzyl)acetylamino]propane, 2-[2-[4-(acetamido)phenoxy]acetyl]-amino-3-(1H-indol-3-yl)-1-[N-(2-methoxybenzyl)acetylamino]propane, 2-[2-[4-(imidazol-1-yl)phenoxy]acetyl]-amino-3-(1H-indol-3-yl)-1-[N-(2-methoxybenzyl)acetylamino]propane, 2-[2-[4-(imidazol-1-yl)phenoxy]acetyl]-amino-3-(1H-indol-3-yl)-1-[N-(2-chlorobenzyl)acetylamino]propane, or 2-[2-[4-(1,2,3-thiadiazol-4-yl)phenoxy]acetyl]-amino-3-(1H-indol-3-yl)-1-[N-(2-methoxybenzyl)acetylamino]propane.

3. A method of treating a condition selected from the group consisting of anxiety, depression, psychosis, schizophrenia, respiratory diseases, inflammatory diseases, neurodegenerative disorders, immunological disorders, gastrointestinal disorders, emesis, and pain, which comprises administering to a mammal in need thereof an effective amount of a compound of the formula

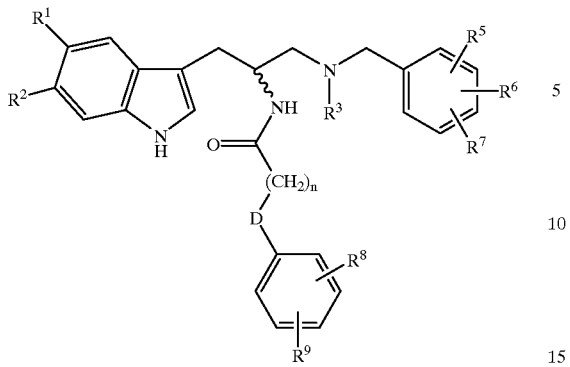

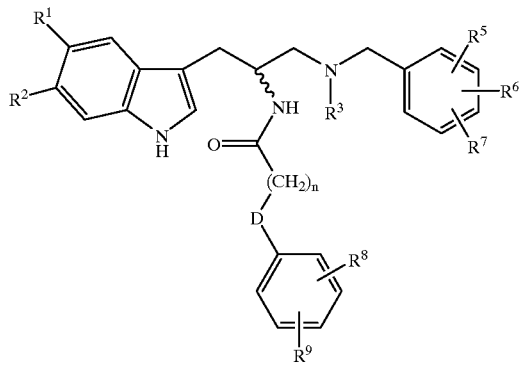

wherein:
- $R^1$ and $R^2$ are independently hydrogen, halo, $C_1$–$C_6$ alkyl, hydroxy, or $C_1$–$C_6$ alkoxy;
- $R^5$, $R^6$, and $R^7$, are independently hydrogen, halo, $C_1$–$C_6$ alkyl, $C_1$–$C_6$ alkoxy, trifluoromethyl, or hydroxy;
- $R^3$ is hydrogen, $C_2$–$C_7$ alkanoyl, glycyl, or dimethylglycyl;
- n is 1–6;
- D is —S(O)$_m$—, —NH—, —C(O)—, or —O—,
  - m is 0, 1, or 2;
- $R^8$ and $R^9$ are independently hydrogen, hydroxy, substituted $C_1$–$C_6$ alkyl, substituted $C_1$–$C_6$ alkoxy, $C_1$–$C_6$ alkylthio, $C_2$–$C_7$ alkoxycarbonyl($C_1$–$C_6$ alkylenyl)-, $C_2$–$C_7$ alkanoyloxy, trifluoromethoxy, trichloromethoxy, $C_1$–$C_6$ alkylthio, formyl, cyano, $R^{10}R^{11}N(C_1$–$C_6$ alkylenyl)-, pyrrolyl, pyrazolinyl, triazolyl, imidazolyl, tetrazolyl, thiazolyl, thiazolinyl, thiadiazolyl, thiadiazolinyl, piperidyl, pyrrolidyl, morpholinyl, morpholinocarbonyl, hexamethyleneiminyl, methylsulfonyl, methylsulfinyl, phenoxy, benzyloxy, carboxy, carbamoyl, or $C_2$–$C_7$ alkylcarbamoyl($C_1$–$C_6$ alkylenyl)-,
  - $R^{10}$ and $R^{11}$ are independently hydrogen or $C_1$–$C_6$ alkyl, said substituted $C_1$–$C_6$ alkyl or substituted $C_1$–$C_6$ alkoxy groups being substituted with one, two, or three moieties selected from the group consisting of hydroxy, acetyl, oxo, halo, cyano, amino, nitro, carboxy, carbamoyl, and thiol;
- or $R^8$ and $R^9$ can combine, together with the benzo ring to which they are attached, to form a naphthyl, dihydronaphthyl, tetrahydronaphthyl, quinolinyl, isoquinolinyl, 2-coumaranonyl, 3-coumaranonyl, benzothiazolyl, benzimidazolyl, indolyl, benzothienyl, benzofuryl, 2,3-dihydrobenzofuryl, indolinyl, or 2,3-dihydrobenzothienyl group, which can be attached to D at any position of the bicyclic group;
- with the proviso that when D is —O— or when m=0, $R^8$ and $R^9$ cannot both be hydrogen;

or a pharmaceutically acceptable salt or solvate thereof.

4. A pharmaceutical formulation, comprising a compound of the formula wherein:
- $R^1$ and $R^2$ are independently hydrogen, halo, $C_1$–$C_6$ alkyl, hydroxy, or $C_1$–$C_6$ alkoxy;
- $R^5$, $R^6$, and $R^7$, are independently hydrogen, halo, $C_1$–$C_6$ alkyl, $C_1$–$C_6$ alkoxy, trifluoromethyl, or hydroxy;
- $R^3$ is hydrogen, $C_2$–$C_7$ alkanoyl, glycyl, or dimethylglycyl;
- n is 1–6;
- D is —S(O)$_m$—, —NH—, —C(O)—, or —O—,
  - m is 0, 1, or 2;
- $R^8$ and $R^9$ are independently hydrogen, hydroxy, substituted $C_1$–$C_6$ alkyl, substituted $C_1$–$C_6$ alkoxy, $C_1$–$C_6$ alkylthio, $C_2$–$C_7$ alkoxycarbonyl($C_1$–$C_6$ alkylenyl)-, $C_2$–$C_7$ alkanoyloxy, trifluoromethoxy, trichloromethoxy, $C_1$–$C_6$ alkylthio, formyl, cyano, $R^{10}R^{11}N(C_1$–$C_6$ alkylenyl)-, pyrrolyl, pyrazolinyl, triazolyl, imidazolyl, tetrazolyl, thiazolyl, thiazolinyl, thiadiazolyl, thiadiazolinyl, piperidyl, pyrrolidyl, morpholinyl, morpholinocarbonyl, hexamethyleneiminyl, methylsulfonyl, methylsulfinyl, phenoxy, benzyloxy, carboxy, carbamoyl, or $C_2$–$C_7$ alkylcarbamoyl($C_1$–$C_6$ alkylenyl)-,
  - $R^{10}$ and $R^{11}$ are independently hydrogen or $C_1$–$C_6$ alkyl,
  - said substituted $C_1$–$C_6$ alkyl or substituted $C_1$–$C_6$ alkoxy groups being substituted with one, two, or three moieties selected from the group consisting of hydroxy, acetyl, oxo, halo, cyano, amino, nitro, carboxy, carbamoyl, and thiol;
- or $R^8$ and $R^9$ can combine, together with the benzo ring to which they are attached, to form a naphthyl, dihydronaphthyl, tetrahydronaphthyl, quinolinyl, isoquinolinyl, 2-coumaranonyl, 3-coumaranonyl, benzothiazolyl, benzimidazolyl, indolyl, benzothienyl, benzofuryl, 2,3-dihydrobenzofuryl, indolinyl, or 2,3-dihydrobenzothienyl group, which can be attached to D at any position of the bicyclic group; with the proviso that when D is —O— or when m=0, $R^8$ and $R^9$ cannot both be hydrogen;

or a pharmaceutically acceptable salt or solvate thereof.

* * * * *